(12) United States Patent
Braun et al.

(10) Patent No.: US 9,370,184 B2
(45) Date of Patent: Jun. 21, 2016

(54) 6-PYRIDONE-2-CARBAMOYL-AZOLES AND THEIR USE AS HERBICIDES

(71) Applicant: BAYER CROPSCIENCE AG, Monheim (DE)

(72) Inventors: Ralf Braun, Ramberg (DE); Stefan Lehr, Lyons (FR); Arnim Koehn, Klein-Winternheim (DE); Hansjoerg Dietrich, Liederbach am Taunus (DE); Elmar Gatzweiler, Bad Nauheim (DE); Christopher Hugh Rosinger, Hofheim (DE); Dirk Schmutzler, Hattersheim (DE)

(73) Assignee: Bayer Cropscience AG, Monheim (DE)

( * ) Notice: Subject to any disclaimer, the term of this patent is extended or adjusted under 35 U.S.C. 154(b) by 5 days.

(21) Appl. No.: 14/397,676

(22) PCT Filed: Apr. 30, 2013

(86) PCT No.: PCT/EP2013/058968
§ 371 (c)(1),
(2) Date: Oct. 29, 2014

(87) PCT Pub. No.: WO2013/164333
PCT Pub. Date: Nov. 7, 2013

(65) Prior Publication Data
US 2015/0111747 A1 Apr. 23, 2015

(30) Foreign Application Priority Data
May 3, 2012 (EP) .................... 12166629

(51) Int. Cl.
| | | |
|---|---|---|
| *C07D 401/00* | (2006.01) | |
| *C07D 419/00* | (2006.01) | |
| *A01N 43/90* | (2006.01) | |
| *C07D 401/12* | (2006.01) | |
| *C07D 413/12* | (2006.01) | |
| *C07D 471/04* | (2006.01) | |
| *A01N 43/653* | (2006.01) | |
| *A01N 43/713* | (2006.01) | |
| *A01N 43/80* | (2006.01) | |
| *A01N 43/82* | (2006.01) | |
| *C07D 401/14* | (2006.01) | |
| *C07D 405/14* | (2006.01) | |
| *C07D 409/14* | (2006.01) | |
| *C07D 413/14* | (2006.01) | |

(52) U.S. Cl.
CPC .............. *A01N 43/90* (2013.01); *A01N 43/653* (2013.01); *A01N 43/713* (2013.01); *A01N 43/80* (2013.01); *A01N 43/82* (2013.01); *C07D 401/12* (2013.01); *C07D 401/14* (2013.01); *C07D 405/14* (2013.01); *C07D 409/14* (2013.01); *C07D 413/12* (2013.01); *C07D 413/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 4,975,538 A | 12/1990 | Barbachyn et al. | |
| 7,935,716 B2 * | 5/2011 | Arimori ................ | A01N 43/50 514/338 |
| 8,481,749 B2 | 7/2013 | Braun et al. | |
| 9,035,064 B2 * | 5/2015 | Kohn ..................... | A01N 43/82 504/103 |
| 2014/0066301 A1 | 3/2014 | Koehn et al. | |

FOREIGN PATENT DOCUMENTS

| | | |
|---|---|---|
| EP | 0281289 A1 | 9/1988 |
| EP | 2686316 A1 | 1/2014 |
| EP | 2688885 A1 | 1/2014 |
| WO | 2012028579 A1 | 3/2012 |
| WO | 2012039141 A1 | 3/2012 |
| WO | WO 2012039141 A1 * | 3/2012 |
| WO | 2012123416 A1 | 9/2012 |
| WO | 2012126932 A1 | 9/2012 |
| WO | WO 2012/123416 A1 * | 9/2012 |

OTHER PUBLICATIONS

International Search Report received in corresponding PCT/EP2013/058968, mailed Jun. 6, 2013.

* cited by examiner

*Primary Examiner* — Janet L Andres
*Assistant Examiner* — Ben S Michelson
(74) *Attorney, Agent, or Firm* — McBee Moore Woodward Vanik, IP, LLC

(57) ABSTRACT

6-Pyridone-2-carbamoylazoles of the general formula (I) are described as herbicides.

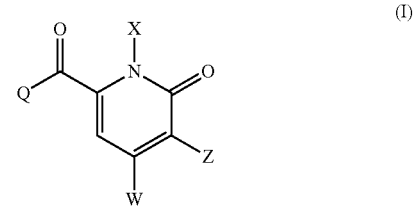

In this formula (I), W, X and Z represent radicals such as hydrogen, organic radicals such as alkyl, and other radicals such as halogen. Q represents a 5-membered radical such as oxadiazyl.

20 Claims, No Drawings

6-PYRIDONE-2-CARBAMOYL-AZOLES AND THEIR USE AS HERBICIDES

CROSS REFERENCE TO RELATED APPLICATIONS

This application is a §371 National Stage Application of PCT/EP2013/058968, filed Apr. 30, 2013, which claims priority to EP 12166629.1, filed May 3, 2012.

BACKGROUND

1. Field of the Invention

The invention relates to the technical field of herbicides, especially that of herbicides for the selective control of broad-leaved weeds and weed grasses in crops of useful plants.

2. Description of Related Art

WO2012/039141 A1 describes 6-pyridone-2-carbonylcyclohexanediones and 6-pyridone-2-carbonylpyrazoles as herbicides. WO 2012/028579 A1 discloses N-(tetrazol-5-yl)- and N-(triazol-5-yl)nicotinamides as herbicides. The application EP 11158253, with an earlier priority date but unpublished at the priority date of the present specification, discloses N-(1,2,5-oxadiazol-3-yl)pyridinecarboxamides as herbicides. The application EP 11159115, with an earlier priority date but unpublished at the priority date of the present specification, discloses N-(1,3,4-oxadiazol-2-yl)nicotinamides as herbicides. However, these active compounds are not always sufficiently active against harmful plants and/or some of them are not sufficiently compatible with some important crop plants such as cereal species, corn or rice.

SUMMARY

Accordingly, it is an object of the present invention to provide further herbicidally active compounds. This object is achieved by the 6-pyridone-2-carbamoylazoles according to the invention described below.

The present invention thus provides 6-pyridone-2-carbamoylazoles of the formula (I) or salts thereof (I)

in which

Q represents a radical $Q^1$, $Q^2$, $Q^3$ or $Q^4$, $Q^1$ $Q^2$ $Q^3$ $Q^4$ $R^3$ represents $(C_1-C_8)$-alkyl, $(C_2-C_8)$-alkenyl, $(C_2-C_8)$-alkynyl, where these radicals are each substituted by s radicals from the group consisting of halogen, cyano, hydroxy, nitro, $SiR^{10}{}_3$, $PO(OR^{10})_2$, $S(O)_n$—$(C_1-C_6)$-alkyl, $(C_1-C_6)$-alkoxy, halo-$(C_1-C_6)$-alkoxy, $COR^{3a}$, $COOR^{3a}$, $OCOR^{3a}$, $NR^{3a}COR^{3a}$, $NR^{3a}SO_2R^{3b}$, $(C_3-C_6)$-cycloalkyl, heteroaryl, heterocyclyl or phenyl, where the 4 last-mentioned radicals are each substituted by p radicals from the group consisting of methyl, ethyl, methoxy, trifluoromethyl, cyano and halogen, and where heterocyclyl carries n oxo groups, or $R^3$ represents phenyl which is substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{3a}$ represents hydrogen, $(C_1-C_6)$-alkyl, $(C_2-C_6)$-alkenyl, $(C_2-C_6)$-alkynyl, $(C_3-C_6)$-cycloalkyl or $(C_3-C_6)$-cycloalkyl-$(C_1-C_6)$-alkyl or phenyl, $R^{3b}$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ represents hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, $(C_1-C_6)$-alkoxy-$(C_1-C_6)$-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or heteroaryl, heterocyclyl or phenyl, each of which is substituted by p radicals from the group consisting of methyl, ethyl, methoxy, trifluoromethyl and halogen, $R^5$ represents hydrogen, $(C_1-C_6)$-alkyl, $(C_1-C_6)$-alkoxy-$(C_1-C_6)$-alkyl, $CH_2R^{5a}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^6$, $NHR^6$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl or represents heteroaryl, heterocyclyl, benzyl or phenyl, each of which is substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{5a}$ represents acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl, or represents heteroaryl or heterocyclyl, each of which is substituted by p radicals from the group consisting of methyl, ethyl, methoxy, trifluoromethyl and halogen, X represents $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $OCOOR^6$, $OC(O)N(R^6)_2$, $OR^6$, $OCOR^6$, $OSO_2R^7$, $(C_1-C_6)$-alkyl-$S(O)_nR^7$, $(C_1-C_6)$-alkyl-$OR^6$, $(C_1-C_6)$-alkyl-$OCOR^6$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-CN, $(C_1-C_6)$-alkyl-$SO_2N(R^6)_2$, $(C_1-C_6)$-alkyl-$NR^6COR^6$, $(C_1-C_6)$-alkyl-$NR^6SO_2R^7$, $CH_2P(O)(OR^{10})_2$, $(C_1-C_6)$-alkyl-aryl, $(C_1-C_6)$-alkyl-heteroaryl, $(C_1-C_6)$-alkyl-heterocyclyl, where the three last-mentioned radicals are each substituted by s radicals from the group consisting of halogen, cyano, nitro, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy, and where heterocyclyl carries n oxo groups, Z represents hydrogen, halogen, cyano, thiocyanato, nitro, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_1-C_6)$-alkyl-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^6$, $COOR^6$, $OR^6$, $OCOOR^6$, $NR^6COOR^6$, $C(O)N(R^6)_2$, $NR^6C(O)N(R^6)_2$, $OC(O)N(R^6)_2$, $C(O)NR^6OR^6$, $OSO_2R^7$, $S(O)_nR^7$, $SO_2OR^6$, $SO_2N(R^6)_2$, $NR^6SO_2R^7$, $NR^6COR^6$, $(C_1-C_6)$-alkyl-$S(O)_nR^7$, $(C_1-C_6)$-alkyl-$OR^6$, $(C_1-C_6)$-alkyl-$OCOR^1$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^1SO_2R^7$, $N(R^6)_2$, $P(O)(OR^{10})_2$, heteroaryl, heterocyclyl or phenyl, where the three last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl carries n oxo groups, W represents hydrogen, halogen, $(C_1-C_4)$-alkyl, $(C_1-C_4)$-haloalkyl, $S(O)_nR^{10}$, or Z and W together with the carbon atoms to which they are attached form a five- or six-membered aromatic ring system in which p carbon atoms are replaced by heteroatoms from the group consisting of N, O and S, and which is substituted by q radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_6)$-alkyl, $R^6$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^8$-heteroaryl, $(C_1-C_6)$-alkyl-$NR^8$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^7$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO_2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^9$ represents $(C_1-C_6)$-alkyl, $(C_2-C_6)$-alkenyl, $(C_2-C_6)$-alkynyl or phenyl, $R^{10}$ represents $(C_1-C_4)$-alkyl, n represents 0, 1 or 2, p represents 0, 1, 2 or 3, q represents 0, 1, 2, 3 or 4, s represents 0, 1, 2, 3, 4 or 5.

DETAILED DESCRIPTION OF A PREFERRED EMBODIMENT

In the formula (I) and all the formulae which follow, alkyl radicals having more than two carbon atoms may be straight-chain or branched. Alkyl radicals represent, for example, methyl, ethyl, n- or isopropyl, n-, iso-, tert- or 2-butyl, pentyls, hexyls such as n-hexyl, isohexyl and 1,3-dimethylbutyl. Analogously, alkenyl represents, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl. Alkynyl represents, for example, propargyl, but-2-yn-1-yl, but-3-yn-1-yl, 1-methylbut-3-yn-1-yl. The multiple bond may be in each case in any position of the unsaturated radical. Cycloalkyl represents a carbocyclic saturated ring system having three to six carbon atoms, for example cyclopropyl, cyclobutyl, cyclopentyl or cyclohexyl. Analogously, cycloalkenyl represents a monocyclic alkenyl group having three to six carbon ring members, for example cyclopropenyl, cyclobutenyl, cyclopentenyl and cyclohexenyl, where the double bond may be in any position.

Halogen represents fluorine, chlorine, bromine or iodine.

Heterocyclyl represents a saturated, semisaturated or fully unsaturated cyclic radical containing 3 to 6 ring atoms, of which 1 to 4 are from the group consisting of oxygen, nitrogen and sulfur, and which may additionally be fused by a benzo ring. For example, heterocyclyl represents piperidinyl, pyrrolidinyl, tetrahydrofuranyl, dihydrofuranyl and oxetanyl.

Heteroaryl represents an aromatic cyclic radical containing 3 to 6 ring atoms, of which 1 to 4 are from the group consisting of oxygen, nitrogen and sulfur, and which may additionally be fused by a benzo ring. For example, heteroaryl represents benzimidazol-2-yl, furanyl, imidazolyl, isoxazolyl, isothiazolyl, oxazolyl, pyrazinyl, pyrimidinyl, pyridazinyl, pyridinyl, benzisoxazolyl, thiazolyl, pyrrolyl, pyrazolyl, thiophenyl, 1,2,3-oxadiazolyl, 1,2,4-oxadiazolyl, 1,2,5-oxadiazolyl, 1,3,4-oxadiazolyl, 1,2,4-triazolyl, 1,2,3-triazolyl, 1,2,5-triazolyl, 1,3,4-triazolyl, 1,2,4-triazolyl, 1,2,4-thiadiazolyl, 1,3,4-thiadiazolyl, 1,2,3-thiadiazolyl, 1,2,5-thiadiazolyl, 2H-1,2,3,4-tetrazolyl, 1H-1,2,3,4-tetrazolyl, 1,2,3,4-oxatriazolyl, 1,2,3,5-oxatriazolyl, 1,2,3,4-thiatriazolyl and 1,2,3,5-thiatriazolyl.

When a group is polysubstituted by radicals, this means that this group is substituted by one or more identical or different radicals from those mentioned.

According to the nature and the bonding of the substituents, the compounds of the general formula (I) may be present as stereoisomers. If, for example, one or more asymmetric carbon atoms are present, there may be enantiomers and diastereomers. Stereoisomers likewise occur when n is 1 (sulfoxides). Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or auxiliaries. The invention also relates to all stereoisomers and mixtures thereof which are encompassed by the general formula (I) but not defined specifically.

The compounds of the formula (I) may form salts. Salts may be formed by action of a base on compounds of the formula (I). Examples of suitable bases are organic amines such as trialkylamines, morpholine, piperidine and pyridine, and the hydroxides, carbonates and hydrogencarbonates of ammonium, alkali metals or alkaline earth metals, in particular sodium hydroxide, potassium hydroxide, sodium carbonate, potassium carbonate, sodium hydrogencarbonate and potassium hydrogencarbonate.

These salts are compounds in which the acidic hydrogen is replaced by an agriculturally suitable cation, for example metal salts, in particular alkali metal salts or alkaline earth metal salts, in particular sodium and potassium salts, or else ammonium salts, salts with organic amines or quaternary ammonium salts, for example with cations of the formula $[NR^aR^bR^cR^d]^+$, in which $R^a$ to $R^d$ in each case independently of one another are an organic radical, in particular alkyl, aryl, aralkyl or alkylaryl. Also useful are alkylsulfonium and alkylsulfoxonium salts, such as $(C_1-C_4)$-trialkylsulfonium and $(C_1-C_4)$-trialkylsulfoxonium salts.

Preference is given to compounds of the general formula (I) in which

Q represents a radical $Q^1$, $Q^2$, $Q^3$ or $Q^4$,

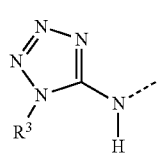

$Q^1$

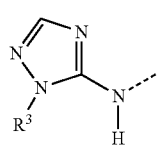

$Q^2$

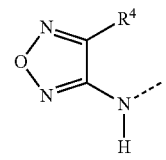

$Q^3$

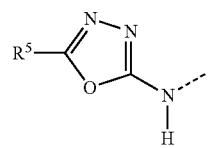

$Q^4$ $R^3$ represents $(C_1-C_8)$-alkyl, $(C_2-C_8)$-alkenyl, $(C_2-C_8)$-alkynyl, where these radicals are each substituted by s radicals from the group consisting of halogen, cyano, nitro, $S(O)_n$—$(C_1-C_6)$-alkyl, $(C_1-C_6)$-alkoxy, halo-$(C_1-C_6)$-alkoxy, $(C_3-C_6)$-cycloalkyl, heteroaryl, heterocyclyl or phenyl, where the 4 last-mentioned radicals are each substituted by p radicals from the group consisting of methyl, ethyl, methoxy, trifluoromethyl, cyano and halogen, and where heterocyclyl carries n oxo groups, or $R^3$ represents phenyl which is in each case substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^4$ represents $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1-yl, pyrazol-1-yl, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or represents phenyl which is in each case substituted by p radicals from the group consisting of methyl, ethyl, methoxy, trifluoromethyl and halogen, $R^5$ represents hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or represents phenyl which is substituted by p radicals from the group consisting of methyl, methoxy, trifluoromethyl and halogen, X represents $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $OCOOR^6$, $OC(O)N(R^6)_2$, $OR^6$, $OCOR^6$, $OSO_2R^7$, $(C_1-C_6)$-alkyl-$S(O)_nR^7$, $(C_1-C_6)$-alkyl-$OR^6$, $(C_1-C_6)$-alkyl-$OCOR^6$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^6SO_2R^7$, $CH_2P(O)(OR^{10})_2$, $(C_1-C_6)$-alkyl-aryl, $(C_1-C_6)$-alkyl-heteroaryl, $(C_1-C_6)$-alkyl-heterocyclyl, where the three last-mentioned radicals are each substituted by s radicals from the group consisting of halogen, cyano, nitro, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Z represents hydrogen, halogen, cyano, thiocyanato, nitro, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^6$, $COOR^6$, $OCOOR^6$, $NR^6COOR^6$, $C(O)N(R^6)_2$, $NR^6C(O)N(R^6)_2$, $OC(O)N(R^6)_2$, $C(O)NR^6OR^6$, $OSO_2R^7$, $S(O)_nR^7$, $SO_2OR^6$, $SO_2N(R^6)_2$, $NR^6SO_2R^7$, $NR^6COR^6$, $(C_1-C_6)$-alkyl-$S(O)_nR^7$, $(C_1-C_6)$-alkyl-$OR^6$, $(C_1-C_6)$-alkyl-$OCOR^1$, $(C_1-C_6)$-alkyl-$OSO_2R'$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^1SO_2R^7$, $N(R^6)_2$, $P(O)(OR^{10})_2$, heteroaryl, heterocyclyl or phenyl, where the last three radicals are in each case substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl carries n oxo groups, W represents hydrogen, halogen, methyl, trifluoromethyl, $S(O)_n Me$, or Z and W together with the carbon atoms to which they are attached form a five- or six-membered aromatic ring system in which p carbon atoms are replaced by heteroatoms from the group consisting of N, O and S, and which is substituted by q radicals from the group consisting of halogen, nitro, cyano, $(C_1-C_6)$-alkyl, halo-$(C_1-C_4)$-alkyl, $(C_3-C_6)$-cycloalkyl, $S(O)_n$—$(C_1-C_6)$-alkyl, $(C_1-C_6)$-alkoxy-$(C_1-C_6)$-alkyl, $(C_1-C_6)$-alkoxy and halo-$(C_1-C_6)$-alkoxy, $R^6$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocycyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^8$-heteroaryl, $(C_1-C_6)$-alkyl-$NR^8$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^7$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO_2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^9$ represents $(C_1-C_6)$-alkyl, $(C_2-C_6)$-alkenyl, $(C_2-C_6)$-alkynyl or phenyl, $R^{10}$ represents $(C_1-C_4)$-alkyl, n represents 0, 1 or 2, p represents 0, 1, 2 or 3, q represents 0, 1, 2, 3 or 4, s represents 0, 1, 2, 3, 4 or 5.

Particular preference is given to compounds of the general formula (I) in which

Q represents a radical $Q^1$, $Q^2$, $Q^3$ or $Q^4$,

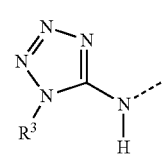

$Q^1$

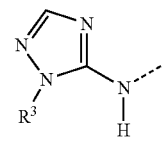

$Q^2$

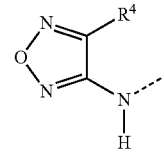

$Q^3$

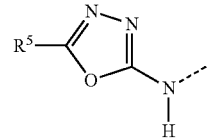

$Q^4$ $R^3$ represents $(C_1-C_8)$-alkyl, $(C_2-C_8)$-alkenyl or $(C_2-C_8)$-alkynyl, each of which is substituted by s radicals from the group consisting of halogen, cyano, nitro, $S(O)_n$—$(C_1-C_6)$-alkyl, $(C_1-C_6)$-alkoxy and halo-$(C_1-C_6)$-alkoxy, $R^4$ represents $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1H, 1-pyrazol-1H, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or represents phenyl which is in each case substituted by s radicals from the group consisting of methyl, ethyl, methoxy, trifluoromethyl and halogen, $R^5$ represents hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or represents phenyl which is substituted by p radicals from the group consisting of methyl, methoxy, trifluoromethyl and halogen;

X represents $(C_1-C_6)$-alkyl, halo-$(C_1-C_6)$-alkyl, $(C_3-C_6)$-cycloalkyl, $OR^6$, $S(O)_nR^7$, $(C_1-C_6)$-alkyl-$S(O)_nR^7$, $(C_1-C_6)$-alkyl-$OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^6SO_2R^7$, $(C_1-C_6)$-alkyl-heteroaryl, $(C_1-C_6)$-alkylheterocyclyl, where the two last-mentioned radicals are in each case substituted by s radicals from the group consisting of halogen, $(C_1-C_6)$- alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Z represents hydrogen, halogen, cyano, thiocyanato, nitro, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^6$, $COOR^6$, $OCOOR^6$, $NR^6COOR^6$, $C(O)N(R^6)_2$, $NR^6C(O)N(R^6)_2$, $OC(O)N(R^6)_2$, $C(O)NR^6OR^6$, $OSO_2R^7$, $S(O)_nR^7$, $SO_2OR^6$, $SO_2N(R^6)_2$, $NR^6SO_2R^7$, $NR^6COR^6$, $(C_1-C_6)$-alkyl-$S(O)_nR^7$, $(C_1-C_6)$-alkyl-$OR^6$, $(C_1-C_6)$-alkyl-$OCOR^1$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^1SO_2R^7$, $N(R^6)_2$, $P(O)(OR^{10})_2$, heteroaryl, heterocyclyl or phenyl, where the 3 last-mentioned radicals are in each case substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl carries n oxo groups, W represents hydrogen, chlorine, methyl or trifluoromethyl, or Z and W together with the carbon atoms to which they are attached form a five- or six-membered aromatic ring system in which p carbon atoms are replaced by heteroatoms from the group consisting of N, O and S, and which is substituted by q radicals from the group consisting of halogen, nitro, cyano, $(C_1-C_6)$-alkyl, halo-$(C_1-C_4)$-alkyl, $S(O)_n$—$(C_1-C_6)$-alkyl, $(C_1-C_6)$-alkoxy-methyl, $(C_1-C_6)$-alkoxy and halo-$(C_1-C_6)$-alkoxy, $R^6$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocycyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^8$-heteroaryl, $(C_1-C_6)$-alkyl-$NR^8$-heterocyclyl, where the 21 last-mentioned radicals are in each case substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^7$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 last-mentioned radicals are each substituted by s radicals from the group consisting of cyano, halogen, nitro, thiocyanato, $OR^8$, $S(O)_n$ $R^9$, $N(R^8)_2$, $NR^8OR^8$, $COR^8$, $OCOR^8$, $SCOR^9$, $NR^8COR^8$, $NR^8SO_2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^9$ represents $(C_1-C_6)$-alkyl, $(C_2-C_6)$-alkenyl, $(C_2-C_6)$-alkynyl or phenyl, $R^{10}$ represents $(C_1-C_4)$-alkyl, n represents 0, 1 or 2, p represents 0, 1, 2 or 3, q represents 0, 1, 2, 3 or 4, s represents 0, 1, 2, 3, 4 or 5.

In all the formulae specified hereinafter, the substituents and symbols have the same meaning as described in formula (I), unless defined differently.

Compounds according to the invention where $Q=Q^1$ or $Q^2$ can be prepared, for example, by the method indicated in WO2012/039141 A1. Compounds according to the invention where $Q=Q^3$ can be prepared, for example, by the method indicated in EP 11158253. Compounds according to the invention where $Q=Q^4$ can be prepared, for example, by the method indicated in EP 11159115.

The 6-pyridone-2-carbonyl chlorides (II) and the 6-pyridone-2-carboxylic acids (III) on which they are based can be prepared, for example, according to Scheme 1:

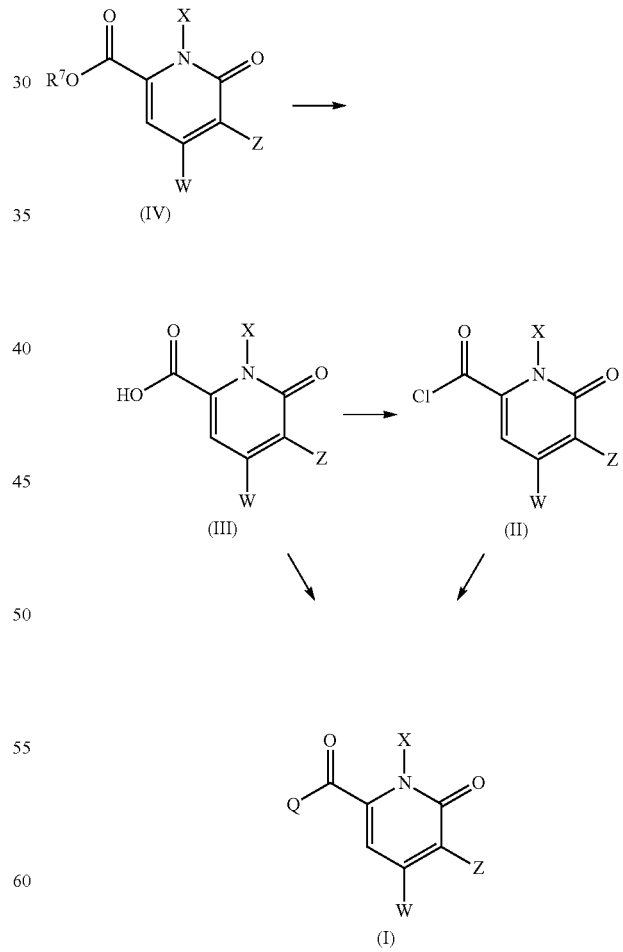

Scheme 1

The 6-pyridone-2-carboxylic esters (IV) can be prepared, for example, according to Scheme 2 from the NH-6-pyridone-2-carboxylic esters (V).

Scheme 2

(V) → (IV)

The 6-pyridone-2-carboxylic esters (IV) can also be prepared, for example, according to Scheme 3 from the 5-hydroxy-6-pyridone-2-carboxylic esters (VI). To this end, initially the hydroxyl group is converted into a sulfonate group, and this is then removed hydrogenolytically with the aid of a catalyst.

Scheme 3

(VI) →

→ (IV)

Compounds (VIII) where X=$OR^6$ can be prepared, for example, according to Scheme 4 by oxidation of the ester (V) to the N-hydroxy compound (VII) according to the method described in *J. Med. Chem* (2002), 45(18), 3963-3971, followed by the introduction of the $R^6$ group.

Scheme 4

(V) →

(VII) → (VIII)

NH-pyrid-6-one-2-carboxylic esters (V) can be prepared, for example, analogously to the methods described in WO 2005/058037 A1.

It may be expedient to change the order of reaction steps. Thus, benzoic acids carrying a sulfoxide cannot be converted directly into their acid chlorides. Here, it is advisable to prepare initially, at the thioether stage, the amide and then to oxidize the thioether to the sulfoxide.

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the work-up or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MultiPROBE Automated Workstations from PerkinElmer, Waltham, Mass. 02451, USA. For the parallelized purification of compounds of the general formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the general formula (I) and salts thereof can be prepared completely or partially by solid-phase supported methods. For this purpose, individual intermediates or all intermediates in the synthesis or a synthesis adapted for the corresponding procedure are bound to a synthesis resin. Solid-phase-supported synthesis methods are described adequately in the technical literature, for example Barry A. Bunin in "The Combinatorial Index", Academic Press, 1998 and Combinatorial Chemistry—Synthesis, Analysis, Screening (editor:

Günther Jung), Wiley, 1999. The use of solid-phase-supported synthesis methods permits a number of protocols, which are known from the literature and which for their part may be performed manually or in an automated manner, to be carried out. The reactions can be performed, for example, by means of IRORI technology in microreactors from Nexus Biosystems, 12140 Community Road, Poway, Calif. 92064, USA.

Both in the solid and in the liquid phase, individual or several synthesis steps may be supported by the use of microwave technology. The specialist literature describes a series of experimental protocols, for example in Microwaves in Organic and Medicinal Chemistry (editor: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The compounds of the formula (I) according to the invention (and/or salts thereof), collectively referred to hereinafter as "compounds according to the invention", have excellent herbicidal efficacy against a broad spectrum of economically important monocotyledonous and dicotyledonous annual weed plants. The active compounds also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more compound(s) according to the invention is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The compounds according to the invention can be deployed, for example, prior to sowing (if appropriate also by incorporation into the soil), prior to emergence or after emergence. Specific examples of some representatives of the monocotyledonous and dicotyledonous weed flora which can be controlled by the compounds according to the invention are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination, either the weed seedlings are prevented completely from emerging or the weeds grow until they have reached the cotyledon stage, but then stop growing and eventually, after three to four weeks have elapsed, die.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* in particular *Zea* and *Triticum,* are damaged only to an insignificant extent, or not at all, depending on the structure of the respective compound according to the invention and its application rate. For these reasons, the present compounds are very suitable for the selective control of unwanted plant growth in plant crops such as agriculturally useful plants or ornamentals.

In addition, the compounds according to the invention (depending on their particular structure and the application rate deployed) have outstanding growth-regulating properties in crop plants. They intervene to regulate the plant's metabolism and can thus be used for controlled influence on plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, this can reduce or completely prevent lodging.

By virtue of their herbicidal and plant-growth-regulating properties, the active compounds can also be used for controlling harmful plants in crops of genetically modified plants or plants modified by conventional mutagenesis. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with an elevated starch content or altered starch quality, or with a different fatty acid composition in the harvested material.

It is preferred, with respect to transgenic crops, to use the compounds according to the invention in economically important transgenic crops of useful plants and ornamentals, for example of cereals such as wheat, barley, rye, oats, millet/sorghum, rice and corn or else crops of sugar beet, cotton, soybean, oilseed rape, potato, tomato, peas and other vegetables. It is preferred to employ the compounds according to the invention as herbicides in crops of useful plants which are resistant, or have been made resistant by recombinant means, to the phytotoxic effects of the herbicides.

Preference is given to the use of the compounds according to the invention or salts thereof in economically important transgenic crops of useful plants and ornamentals, for example of cereals such as wheat, barley, rye, oats, millet/sorghum, rice, cassava and corn, or else crops of sugar beet, cotton, soybean, oilseed rape, potato, tomato, peas and other vegetables. Preferably, the compounds according to the invention can be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with modified properties can be generated with the aid of recombinant methods (see, for example, EP-A-0221044, EP-A-0131624). For example, there have been many descriptions of:

recombinant modifications of crop plants for the purpose of modifying the starch synthesized in the plants (for example WO 92/11376, WO 92/14827, WO 91/19806), transgenic crop plants which are resistant to particular herbicides of the glufosinate type (cf., for example, EP-A-0242236, EP-A-242246) or glyphosate type (WO 92/00377) or of the sulfonylurea type (EP-A-0257993, U.S. Pat. No. 5,013,659), transgenic crop plants, for example cotton, with the ability to produce *Bacillus thuringiensis* toxins (Bt toxins) which make the plants resistant to particular pests (EP-A-0142924, EP-A-0193259), transgenic crop plants with a modified fatty acid composition (WO 91/13972), genetically modified crop plants with novel constituents or secondary metabolites, for example novel phytoalexins, which bring about an increased disease resistance (EPA 309862, EPA0464461), genetically modified plants with reduced photorespiration which feature higher yields and higher stress tolerance (EPA 0305398), transgenic crop plants which produce pharmaceutically or diagnostically important proteins ("molecular pharming"), transgenic crop plants which are distinguished by higher yields or better quality, transgenic crop plants which are distinguished by a combination, for example of the abovementioned novel properties ("gene stacking")

A large number of molecular-biological techniques by means of which novel transgenic plants with modified properties can be generated are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or a sequence change by recombination of DNA sequences can be introduced into plasmids. With the aid of standard methods, it is possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene and Klone" [Genes and Clones], VCH Weinheim 2nd edition 1996.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product. To this end, it is possible to use DNA molecules which encompass the entire coding sequence of a gene product inclusive of any flanking sequences which may be present, and also DNA molecules which only encompass portions of the coding sequence, it being necessary for these portions to be long enough to have an antisense effect in the cells. The use of DNA sequences which have a high degree of homology to the coding sequences of a gene product, but are not completely identical to them, is also possible.

When expressing nucleic acid molecules in plants, the protein synthesized may be localized in any desired compartment of the plant cell. However, in order to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants.

For instance, it is possible to obtain transgenic plants whose properties are altered by overexpression, suppression or inhibition of homologous (=natural) genes or gene sequences, or expression of heterologous (=foreign) genes or gene sequences.

Preferably, the compounds according to the invention can be used in transgenic crops which are resistant to growth regulators, for example dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active compounds.

On employment of the active compounds according to the invention in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants. The invention therefore also provides for the use of the compounds according to the invention as herbicides for control of weed plants in transgenic crop plants.

The compounds according to the invention can be applied in the form of wettable powders, emulsifiable concentrates, sprayable solutions, dusting products or granules in the customary formulations. The invention therefore also provides herbicidal and plant growth-regulating compositions which comprise the compounds according to the invention.

The compounds according to the invention can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives, are likewise known and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-Küchler, "Chemische Technologie" [Chemical Technology], volume 7, C. Hanser Verlag Munich, 4th ed. 1986.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyethoxylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To prepare the wettable powders, the herbicidally active compounds are ground finely, for example in customary apparatus such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Emulsifiers used may, for example, be: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusts are obtained by grinding the active compound with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active substance onto adsorptive granular inert material or by applying active substance concentrates to the surface of carriers, such as sand, kaolinites or granular inert material, by means of adhesives, for example polyvinyl alcohol, sodium polyacrylates or mineral oils. Suitable active compounds can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London, J. E. Browning, "Agglomeration", Chemical and Engineering 1967, pages 147 ff.; "Perry's Chemical Engineer's Handbook", 5th ed., McGraw-Hill, New York 1973, pp. 8-57.

For further details regarding the formulation of crop protection agents, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of compounds according to the invention.

In wettable powders, the active compound concentration is, for example, about 10 to 90% by weight, the remainder to 100% by weight consisting of customary formulation constituents. In emulsifiable concentrates, the active ingredient concentration may be about 1 to 90% and preferably 5 to 80% by weight. Formulations in the form of dusts comprise 1 to 30% by weight of active compound, preferably usually 5 to 20% by weight of active compound; sprayable solutions contain about 0.05 to 80, preferably 2 to 50, % by weight of active compound. In the case of water-dispersible granules, the active compound content depends partly on whether the active compound is present in liquid or solid form and on which granulation assistants, fillers, etc., are used. In the water-dispersible granules, the content of active compound is, for example, between 1 and 95% by weight, preferably between 10 and 80% by weight.

In addition, the active compound formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

Based on these formulations, it is also possible to produce combinations with other pesticidally active compounds, such as, for example, insecticides, acaricides, herbicides, fungicides, and also with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Preparations in the form of dusts, granules for soil application or granules for sowing and sprayable solutions are usually not diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

The examples below illustrate the invention.

A. CHEMICAL EXAMPLES

1. Synthesis of 5-chloro-1-methyl-N-(1-methyltetrazol-5-yl)pyrid-6-one-2-carboxamide, (Table Example No. 1-31)

At 0° C., 9.45 g (75 mmol) of dimethyl sulfate are added to 11.24 g (60 mmol) of methyl 5-chloropyrid-6-one-2-carboxylate and 10.36 g (75 mmol) of potassium carbonate in 60 ml of DMF. The mixture is allowed to warm to room temperature (RT), and after 16 h water and ethyl acetate are added. The organic phase is washed repeatedly with water, then with sat. sodium bicarbonate solution and with brine. After drying and concentration, the residue is purified by column chromatography using heptane/ethyl acetate.

Fraction A 3.88 g (yield 32%) of methyl 5-chloro-6-methoxypyridine-2-carboxylate Fraction B 5.18 g (yield 43%) of methyl 5-chloro-1-methylpyrid-6-one-2-carboxylate At 0° C., 584 mg (7.5 mmol) of sodium thiomethoxide are added to 604 mg (3 mmol) of methyl 5-chloro-1-methylpyrid-6-one-2-carboxylate in 6 ml of DMF. The mixture is allowed to warm to RT, and after 3 h 2N HCl and ethyl acetate are added. The organic phase is washed repeatedly with water, then with brine. Drying and concentration gives 5-methylsulfenyl-1-methylpyrid-6-one-2-carboxylic acid. Yield 236 mg (40%). At 0° C., 173 mg (1.45 mmol) of thionyl chloride are added to 231 mg (1.16 mmol) of 5-methylsulfenyl-1-methylpyrid-6-one-2-carboxylic acid and 176 mg (1.74 mmol) of 1-methyl-5-aminotetrazole in 3 ml of pyridine. The mixture is stirred at RT for 16 h. The reaction is then quenched with a little water, the pyridine is evaporated and the residue is purified by HPLC. Yield 74 mg (23%).

2. Synthesis of N-(1-methyltetrazol-5-yl)-1-methoxy-5-trifluoromethylpyrid-6-one-2-carboxamide, (Table Example No. 1-25)

A mixture of 0.8 ml of $H_2O_2$ (30% strength) in 3 ml of acetic acid is added to 1.4 g (6 mmol) of methyl 5-trifluoromethylpyrid-6-one-2-carboxylate in 5 ml of trifluoroacetic acid and 4 ml of acetic acid, and the mixture is heated at 80° C. for 12 h. The mixture is then diluted with ethyl acetate, and washed with 2N sodium bisulfite solution and repeatedly with brine. Drying and concentration gives methyl 1-hydroxy-5-trifluoromethylpyrid-6-one-2-carboxylate which is reacted further without purification. At 0° C., 1.89 g (15 mmol) of dimethyl sulfate are added to the residue and 2.1 g (15 mmol) of potassium carbonate in 10 ml of DMF. The mixture is allowed to warm to RT, and after 2 h water, 2N HCl and ethyl acetate are added. The organic phase is washed repeatedly with water, then with sat. sodium bicarbonate solution and with brine. After drying and concentration, the methyl 1-methoxy-5-trifluoromethylpyrid-6-one-2-carboxylate is reacted further without purification. At 0° C., 5 ml of 2N NaOH are added to the residue in 5 ml of methanol, and after 30 min the mixture is acidified with 2N HCl. The mixture is diluted with ethyl acetate, the phases are separated and the organic phase is washed repeatedly with brine. Drying and concentration gives 1-methoxy-5-trifluoromethylpyrid-6-one-2-carboxylic acid. Yield 830 mg (58%).

At 0° C., 149 mg (1.25 mmol) of thionyl chloride are added to 237 mg (1.0 mmol) of 1-methoxy-5-trifluoromethylpyrid-6-one-2-carboxylic acid and 147 mg (1.5 mmol) of 1-methyl-5-aminotetrazole in 3 ml of pyridine. The mixture is stirred at RT for 16 h. 2N HCl and ethyl acetate are then added, the phases are separated and the organic phase is washed repeatedly with brine. After drying and concentration, the residue is purified by HPLC. Yield 122 mg (38%).

3. Synthesis of 1-benzyl-5-trifluoromethyl-N-(1-methyltetrazol-5-yl)pyrid-6-one-2-carboxamide, (Table Example No. 1-15)

At 0° C., 1.3 ml (11 mmol) of benzyl bromide are added to 2.21 g (10 mmol) of methyl 5-trifluoromethylpyrid-6-one-2-carboxylate and 2.07 g (15 mmol) of potassium carbonate in 10 ml of DMF. The mixture is allowed to warm to RT, and after 5 h water and ethyl acetate are added. The organic phase is washed repeatedly with water, then with saturated $NaHCO_3$ solution and with brine. After drying and concentration, the residue is purified by column chromatography using heptane/ethyl acetate.

Fraction A 1.55 g (yield 50%) of methyl 6-benzyloxy-5-trifluoromethylpyridine-2-carboxylate Fraction B 1.19 g (yield 38%) of methyl 1-benzyl-5-trifluoromethylpyrid-6-one-2-carboxylate 4 ml of 2N aqueous sodium hydroxide solution are added to 1.19 g (3.9 mmol) of methyl 1-benzyl-5-trifluoromethylpyrid-6-one-2-carboxylate in 8 ml of MeOH, and after 30 min the mixture is acidified with 2N HCl. The mixture is diluted with ethyl acetate and, after phase separation, washed repeatedly with brine. Drying and concentration gives 1-benzyl-5-trifluoromethylpyrid-6-one-2-carboxylic acid.

At 0° C., 155 mg (1.3 mmol) of thionyl chloride are added to 297 mg (1 mmol) of 1-benzyl-5-trifluoromethylpyrid-6-one-2-carboxylic acid and 149 mg (1.5 mmol) of 1-methyl-5-aminotetrazole in 3 ml of pyridine. The mixture is stirred at RT for 16 h. 2N HCl and ethyl acetate are then added, the phases are separated and the organic phase is washed repeatedly with brine. After drying and concentration, the residue is purified by HPLC. Yield 277 mg (73%).

4. Synthesis of 7-methyl-N-(1-methyltetrazol-5-yl)-1,7-naphthyridin-8(7H)-one-6-carboxamide, (Table Example No. 5-3)

At room temperature, 375 mg (1.05 mmol) of N-phenylbis(trifluoromethanesulfonimide) are added to 234 mg (1 mmol) of methyl 5-hydroxy-7-methyl-1,7-naphthyridin-8(7H)-one-6-carboxylate (J. Heterocyclic Chem. (1999), 36, 979-984) and 111 mg (1.1 mmol) of triethylamine in 3 ml of DCM. After 1 h, the mixture is quenched with saturated $NaHCO_3$ solution. The organic phase is separated off, dried and concentrated. The residue is dissolved in 8 ml of ethanol, 164 mg (2 mmol) of sodium acetate and 10 mg of Pd/C (10%) are added and the mixture is stirred under an atmosphere of hydrogen for 8 h. The catalyst is then filtered off and the solution is concentrated and taken up in sat. NaHCO$_3$ solution and DCM. The org. phase is separated off, dried and concentrated and the residue is purified by column chromatography using heptane/ethyl acetate. Yield 100 mg (46%) of methyl 7-methyl-1,7-naphthyridin-8(7H)-one-6-carboxylate.

100 mg of methyl 7-methyl-1,7-naphthyridin-8(7H)-one-6-carboxylate in 2 ml of methanol and 1 ml of 2N aqueous sodium hydroxide solution are stirred for 3 h, the mixture is acidified with 2N hydrochloric acid and the crystals obtained are filtered off with suction. Yield 60 mg (64%) of 7-methyl-1,7-naphthyridin-8(7H)-one-6-carboxylic acid.

At 0° C., 114 mg (0.96 mmol) of thionyl chloride are added to 150 mg (0.74 mmol) of 7-methyl-1,7-naphthyridin-8(7H)-one-6-carboxylic acid and 110 mg (1.1 mmol) of 1-methyl-5-aminotetrazole in 3 ml of pyridine. The mixture is stirred at RT for 16 h. The reaction is then quenched with a little water, the pyridine is evaporated and the residue is purified by HPLC. Yield 27 mg (13%).

The examples listed in the tables below were prepared analogously to the methods mentioned above or can be obtained analogously to the methods mentioned above. These compounds are very particularly preferred.

The abbreviations used mean:

Et=ethyl  Me=methyl  nPr=n-propyl  cPr=cyclopropyl  Bn=benzyl  Ph=phenyl

TABLE 1

Compounds of the general formula (I) according to the invention, in which Q represents Q$^1$

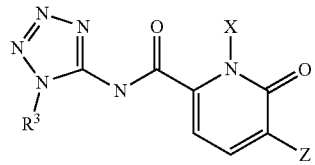

| No. | R$^3$ | X | Z | Physical data ($^1$H-NMR, DMSO-d$_6$, 400 MHz) |
|---|---|---|---|---|
| 1-1 | Me | Me | H | 12.05 (brs, 1H), 7.53 (dd, 1H), 6.72 (brd, 1H), 6.63 (dd, 1H), 3.98 (s, 3H), 3.47 (s, 3H) |
| 1-2 | Me | Me | Me | 11.93 (brs, 1H), 7.43 (dd, 1H), 6.79 (d, 1H), 3.98 (s, 3H), 3.49 (s, 3H), 2.08 (d, 3H) |
| 1-3 | Me | Me | CF$_3$ | 8.15 (d, 1H), 6.69 (d, 1H), 3.99 (s, 3H), 3.82 (s, 3H) |
| 1-4 | Et | Me | CF$_3$ | 7.90 (d, 1H), 6.41 (d, 1H), 4.14 (q, 2H), 3.53 (s, 3H), 1.35 (t, 3H) |
| 1-5 | nPr | Me | CF$_3$ | 7.87 (d, 1H), 6.33 (d, 1H), 4.04 (m, 2H), 3.53 (s, 3H), 1.76 (m, 2H), 0.84 (t, 3H) |
| 1-6 | C$_2$H$_4$OCH$_3$ | Me | CF$_3$ | 7.87 (d, 1H), 6.33 (d, 1H), 4.46 (t, 2H), 3.68 (t, 2H), 3.52 (s, 3H), 3.21 (s, 3H) |
| 1-7 | Me | Et | CF$_3$ | 12.3 (brs, 1H), 8.11 (d, 1H), 6.83 (d, 1H), 4.05 (q, 2H), 4.01 (s, 3H), 1.28 (t, 3H) |
| 1-8 | Et | Et | CF$_3$ | |
| 1-9 | nPr | Et | CF$_3$ | |
| 1-10 | C$_2$H$_4$OCH$_3$ | Et | CF$_3$ | |
| 1-11 | Me | CH$_2$cPr | CF$_3$ | 12.35 (brs, 1H), 8.12 (d, 1H), 6.88 (d, 1H), 4.01 (d, 2H), 4.00 (s, 3H), 1.22 (m, 1H), 0.48 (m, 2H), 0.38 (m, 2H) |
| 1-12 | Et | CH$_2$cPr | CF$_3$ | |
| 1-13 | nPr | CH$_2$cPr | CF$_3$ | |
| 1-14 | C$_2$H$_4$OCH$_3$ | CH$_2$cPr | CF$_3$ | |
| 1-15 | Me | Bn | CF$_3$ | 7.94 (d, 1H), 7.28-7.21 (m, 5H), 6.53 (d, 1H), 5.55 (s, 2H), 3.52 (s, 3H) |
| 1-16 | Et | Bn | CF$_3$ | |
| 1-17 | nPr | Bn | CF$_3$ | |
| 1-18 | C$_2$H$_4$OCH$_3$ | Bn | CF$_3$ | |
| 1-19 | Me | C$_2$H$_4$OCH$_3$ | CF$_3$ | 12.2 (brs, 1H), 8.12 (d, 1H), 6.88 (d, 1H), 4.43 (t, 2H), 3.99 (s, 3H), 3.52 (t, 2H), 3.22 (s, 3H) |
| 1-20 | Et | C$_2$H$_4$OCH$_3$ | CF$_3$ | |
| 1-21 | nPr | C$_2$H$_4$OCH$_3$ | CF$_3$ | |
| 1-22 | C$_2$H$_4$OCH$_3$ | C$_2$H$_4$OCH$_3$ | CF$_3$ | |
| 1-23 | Me | allyl | CF$_3$ | 12.25 (brs, 1H), 8.17 (d, 1H), 6.89 (d, 1H), 5.91 (ddt, 1H), 5.22 (d, 1H), 5.07 (d, 1H), 4.77 (d, 2H), 3.98 (s, 3H), 3.42 (t, 1H) |
| 1-24 | Me | propargyl | CF$_3$ | 8.17 (d, 1H), 6.98 (d, 1H), 4.99 (d, 2H), 4.01 (s, 3H), 3.42 (t, 1H) |
| 1-25 | Me | OMe | CF$_3$ | 12.3 (brs, 1H), 8.13 (d, 1H), 6.84 (d, 1H), 4.09 (s, 3H), 4.00 (s, 3H) |
| 1-26 | Et | OMe | CF$_3$ | |
| 1-27 | nPr | OMe | CF$_3$ | |
| 1-28 | C$_2$H$_4$OCH$_3$ | OMe | CF$_3$ | |
| 1-29 | Me | Me | Ph | 12.06 (brs, 1H), 7.75-7.7 (m, 3H), 7.43-7.36 (m, 3H), 6.85 (d, 1H), 4.01 (s, 3H), 3.56 (s, 3H) |
| 1-30 | Me | Me | OMe | |
| 1-31 | Me | Me | Cl | 12.1 (brs, 1H), 7.91 (d, 1H), 6.78 (d, 1H), 3.99 (s, 3H), 3.56 (s, 3H) |

TABLE 1-continued

Compounds of the general formula (I) according to the invention, in which Q represents $Q^1$

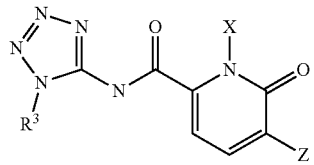

| No. | $R^3$ | X | Z | Physical data ($^1$H-NMR, DMSO-$d_6$, 400 MHz) |
|---|---|---|---|---|
| 1-32 | Et | Me | Cl | |
| 1-33 | nPr | Me | Cl | |
| 1-34 | C$_2$H$_4$OCH$_3$ | Me | Cl | |
| 1-35 | Me | Bn | Cl | |
| 1-36 | Et | Bn | Cl | |
| 1-37 | nPr | Bn | Cl | |
| 1-38 | C$_2$H$_4$OCH$_3$ | Bn | Cl | |
| 1-39 | Me | OMe | Cl | 12.2 (brs, 1H), 7.94 (d, 1H), 6.75 (d, 1H), 4.08 (s, 3H), 3.98 (s, 3H) |
| 1-40 | Et | OMe | Cl | |
| 1-41 | nPr | OMe | Cl | |
| 1-42 | C$_2$H$_4$OCH$_3$ | OMe | Cl | |
| 1-43 | Me | Et | Cl | |
| 1-44 | Et | Et | Cl | |
| 1-45 | nPr | Et | Cl | |
| 1-46 | C$_2$H$_4$OCH$_3$ | Et | Cl | |
| 1-47 | Me | CH$_2$cPr | Cl | |
| 1-48 | Et | CH$_2$cPr | Cl | |
| 1-49 | nPr | CH$_2$cPr | Cl | |
| 1-50 | C$_2$H$_4$OCH$_3$ | CH$_2$cPr | Cl | |
| 1-51 | Me | C$_2$H$_4$OCH$_3$ | Cl | |
| 1-52 | Et | C$_2$H$_4$OCH$_3$ | Cl | |
| 1-53 | nPr | C$_2$H$_4$OCH$_3$ | Cl | |
| 1-54 | C$_2$H$_4$OCH$_3$ | C$_2$H$_4$OCH$_3$ | Cl | |
| 1-55 | Me | Me | Br | 12.1 (brs, 1H), 8.09 (d, 1H), 6.69 (d, 1H), 3.99 (s, 3H), 3.55 (s, 3H) |
| 1-56 | Me | Me | SMe | 11.92 (brs, 1H), 7.22 (d, 1H), 6.87 (d, 1H), 3.97 (s, 3H), 3.54 (s, 3H), 2.38 (s, 3H) |
| 1-57 | Et | Me | SMe | |
| 1-58 | nPr | Me | SMe | |
| 1-59 | C$_2$H$_4$OCH$_3$ | Me | SMe | |
| 1-60 | Me | Bn | SMe | |
| 1-61 | Et | Bn | SMe | |
| 1-62 | nPr | Bn | SMe | |
| 1-63 | C$_2$H$_4$OCH$_3$ | Bn | SMe | |
| 1-64 | Me | OMe | SMe | |
| 1-65 | Et | OMe | SMe | |
| 1-66 | nPr | OMe | SMe | |
| 1-67 | C$_2$H$_4$OCH$_3$ | OMe | SMe | |
| 1-68 | Me | Me | SEt | 11.90 (brs, 1H), 7.30 (d, 1H), 6.84 (d, 1H), 3.97 (s, 3H), 3.53 (s, 3H), 2.91 (q, 2H), 1.29 (t, 3H) |
| 1-69 | Et | Me | SEt | |
| 1-70 | nPr | Me | SEt | |
| 1-71 | C$_2$H$_4$OCH$_3$ | Me | SEt | |
| 1-72 | Me | Bn | SEt | |
| 1-73 | Et | Bn | SEt | |
| 1-74 | nPr | Bn | SEt | |
| 1-75 | C$_2$H$_4$OCH$_3$ | Bn | SEt | |
| 1-76 | Me | OMe | SEt | |
| 1-77 | Et | OMe | SEt | |
| 1-78 | nPr | OMe | SEt | |
| 1-79 | C$_2$H$_4$OCH$_3$ | OMe | SEt | |
| 1-80 | Me | Me | SO$_2$Me | 12.28 (brs, 1H), 8.23 (d, 1H), 6.91 (d, 1H), 4.01 (s, 3H), 3.57 (s, 3H), 3.31 (s, 3H) |
| 1-81 | Et | Me | SO$_2$Me | |
| 1-82 | nPr | Me | SO$_2$Me | |
| 1-83 | C$_2$H$_4$OCH$_3$ | Me | SO$_2$Me | |
| 1-84 | Me | Bn | SO$_2$Me | |
| 1-85 | Et | Bn | SO$_2$Me | |
| 1-86 | nPr | Bn | SO$_2$Me | |
| 1-87 | C$_2$H$_4$OCH$_3$ | Bn | SO$_2$Me | |
| 1-88 | Me | OMe | SO$_2$Me | |
| 1-89 | Et | OMe | SO$_2$Me | |
| 1-90 | nPr | OMe | SO$_2$Me | |
| 1-91 | C$_2$H$_4$OCH$_3$ | OMe | SO$_2$Me | |

TABLE 1-continued

Compounds of the general formula (I) according to the invention, in which Q represents $Q^1$

| No. | $R^3$ | X | Z | Physical data ($^1$H-NMR, DMSO-$d_6$, 400 MHz) |
|---|---|---|---|---|
| 1-92 | Me | Me | $SO_2Et$ | 12.25 (brs, 1H), 8.23 (d, 1H), 6.91 (d, 1H), 4.00 (s, 3H), 3.56 (s, 3H), 3.49 (q, 2H), 1.13 (t, 3H) |
| 1-93 | Et | Me | $SO_2Et$ | |
| 1-94 | nPr | Me | $SO_2Et$ | |
| 1-95 | $C_2H_4OCH_3$ | Me | $SO_2Et$ | |
| 1-96 | Me | Bn | $SO_2Et$ | |
| 1-97 | Et | Bn | $SO_2Et$ | |
| 1-98 | nPr | Bn | $SO_2Et$ | |
| 1-99 | $C_2H_4OCH_3$ | Bn | $SO_2Et$ | |
| 1-100 | Me | OMe | $SO_2Et$ | |
| 1-101 | Et | OMe | $SO_2Et$ | |
| 1-102 | nPr | OMe | $SO_2Et$ | |
| 1-103 | $C_2H_4OCH_3$ | OMe | $SO_2Et$ | |
| 1-104 | Me | $CH_2$(3,4-methylenedioxyphenyl) | $CF_3$ | 12.20 (brs, 1H), 8.18 (d, 1H), 6.92 (d, 1H), 6.85 (d, 1H), 6.76 (d, 1H), 6.67 (dd, 1H), 5.99 (s, 2H), 5.28 (s, 2H), 3.90 (s, 3H) |
| 1-105 | Et | $CH_2$(3,4-methylenedioxyphenyl) | $CF_3$ | 12.10 (brs, 1H), 8.17 (d, 1H), 6.91 (d, 1H), 6.86 (d, 1H), 6.76 (d, 1H), 6.66 (d, 1H), 6.00 (s, 2H), 5.30 (s, 2H), 4.18 (q, 2H), 1.38 (t, 3H) |
| 1-106 | Me | $CH_2$(3-methylisoxazol-5-yl) | $CF_3$ | 12.30 (brs, 1H), 8.21 (d, 1H), 6.99 (d, 1H), 6.24 (s, 1H), 5.47 (s, 2H), 3.96 (s, 3H), 2.19 (s, 3H) |
| 1-107 | Me | $CH_2$(3,5-dimethylpyrazol-1-yl) | $CF_3$ | 12.37 (brs, 1H), 8.19 (d, 1H), 6.97 (d, 1H), 6.39 (s, 2H), 5.81 (1, 2H), 4.07 (s, 3H), 2.38 (s, 3H), 2.06 (s, 3H) |
| 1-108 | Me | $CH_2$(thiophen-2-yl) | $CF_3$ | 12.27 (brs, 1H), 8.16 (d, 1H), 7.48 (dd, 1H), 7.04 (dd, 1H), 6.97 (dd, 1H), 6.92 (d, 1H), 5.53 (s, 2H), 3.96 (s, 3H) |
| 1-109 | Me | Me | 3,5-$F_2$—Ph | 12.12 (brs, 1H), 7.93 (d, 1H), 7.56 (ddd, 2H), 7.26 (dt, 1H), 6.87 (d, 1H), 4.01 (s, 3H), 3.57 (s, 3H) |
| 1-110 | Me | $CHF_2$ | $CF_3$ | |
| 1-111 | Me | Me | cPr | |

TABLE 2

Compounds of the general formula (I) according to the invention, in which Q represents $Q^2$ and $R^3$ represents methyl

| No. | X | Z | Physical data ($^1$H-NMR, DMSO-$d_6$, 400 MHz) |
|---|---|---|---|
| 2-1 | Me | $CF_3$ | 11.7 (brs, 1H), 8.05 (brs, 1H), 7.95 (brs, 1H), 6.78 (brs, 1H), 3.76 (brs, 3H), 3.54 (s, 3H) |
| 2-2 | Et | $CF_3$ | 11.7 (brs, 1H), 8.13 (brs, 1H), 8.04 (d, 1H), 6.72 (d, 1H), 4.09 (q, 2H), 3.54 (s, 3H), 1.35 (t, 3H) |
| 2-3 | $CH_2cPr$ | $CF_3$ | |
| 2-4 | $C_2H_4OCH_3$ | $CF_3$ | |
| 2-5 | Bn | $CF_3$ | |
| 2-6 | $CH_2$(3,4-methylenedioxyphenyl) | $CF_3$ | 8.08 (brd, 2H), 6.83 (d, 1H), 6.79 (brs, 2H), 6.69 (d, 1H), 5.98 (s, 2H), 5.33 (s, 2H), 3.62 (s, 3H) |
| 2-7 | OMe | $CF_3$ | |
| 2-8 | Me | Cl | |
| 2-9 | Et | Cl | |
| 2-10 | $CH_2cPr$ | Cl | |

TABLE 2-continued

Compounds of the general formula (I) according to the invention, in which Q represents $Q^2$ and $R^3$ represents methyl

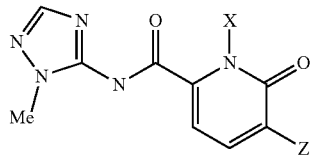

| No. | X | Z | Physical data ($^1$H-NMR, DMSO-$d_6$, 400 MHz) |
|---|---|---|---|
| 2-11 | C$_2$H$_4$OCH$_3$ | Cl | |
| 2-12 | Bn | Cl | |
| 2-13 | OMe | Cl | |
| 2-14 | Me | SMe | |
| 2-15 | Et | SMe | |
| 2-16 | CH$_2$cPr | SMe | |
| 2-17 | C$_2$H$_4$OCH$_3$ | SMe | |
| 2-18 | Bn | SMe | |
| 2-19 | OMe | SMe | |

TABLE 3

Compounds of the general formula (I) according to the invention, in which Q represents

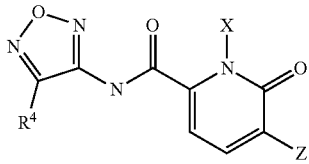

| No. | R$^4$ | X | Z | Physical data ($^1$H-NMR, DMSO-$d_6$, 400 MHz) |
|---|---|---|---|---|
| 3-1 | Me | Me | CF$_3$ | 11.84 (brs, 1H), 8.10 (d, 1H), 6.76 (d, 1H), 3.51 (s, 3H), 2.40 (s, 3H) |
| 3-2 | Cl | Me | CF$_3$ | 12.2 (brs, 1H), 8.09 (d, 1H), 6.72 (d, 1H), 3.50 (s, 3H) |
| 3-3 | Me | Et | CF$_3$ | |
| 3-4 | Cl | Et | CF$_3$ | |
| 3-5 | Me | CH$_2$cPr | CF$_3$ | |
| 3-6 | Cl | CH$_2$cPr | CF$_3$ | |
| 3-7 | Me | C$_2$H$_4$OCH$_3$ | CF$_3$ | |
| 3-8 | Cl | C$_2$H$_4$OCH$_3$ | CF$_3$ | |
| 3-9 | Me | Bn | CF$_3$ | |
| 3-10 | Cl | Bn | CF$_3$ | |
| 3-11 | Me | OMe | CF$_3$ | |
| 3-12 | Cl | OMe | CF$_3$ | |
| 3-13 | Me | Me | Cl | |
| 3-14 | Cl | Me | Cl | |
| 3-15 | Me | Et | Cl | |
| 3-16 | Cl | Et | Cl | |
| 3-17 | Me | CH$_2$cPr | Cl | |
| 3-18 | Cl | CH$_2$cPr | Cl | |
| 3-19 | Me | C$_2$H$_4$OCH$_3$ | Cl | |
| 3-20 | Cl | C$_2$H$_4$OCH$_3$ | Cl | |
| 3-21 | Me | Bn | Cl | |
| 3-22 | Cl | Bn | Cl | |
| 3-23 | Me | OMe | Cl | |
| 3-24 | Cl | OMe | Cl | |
| 3-25 | Me | Me | SMe | |
| 3-26 | Me | Me | SO$_2$Me | |
| 3-27 | Me | Me | SEt | |
| 3-28 | Me | Me | SO$_2$Et | |
| 3-29 | Cl | Me | SMe | |
| 3-30 | Me | Et | SMe | |
| 3-31 | Cl | Et | SMe | |
| 3-32 | Me | CH$_2$cPr | SMe | |
| 3-33 | Cl | CH$_2$cPr | SMe | |

TABLE 3-continued

Compounds of the general formula (I) according to the invention, in which Q represents

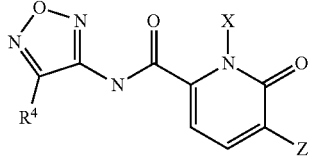

| No. | $R^4$ | X | Z | Physical data ($^1$H-NMR, DMSO-$d_6$, 400 MHz) |
|---|---|---|---|---|
| 3-34 | Me | $C_2H_4OCH_3$ | SMe | |
| 3-35 | Cl | $C_2H_4OCH_3$ | SMe | |
| 3-36 | Me | Bn | SMe | |
| 3-37 | Cl | Bn | SMe | |
| 3-38 | Me | OMe | SMe | |
| 3-39 | Cl | OMe | SMe | |
| 3-40 | Me | $CH_2$(3,4-methylenedioxyphenyl) | $CF_3$ | 11.77 (brs, 1H), 8.15 (d, 1H), 6.83 (d, 1H), 6.82 (d, 1H), 6.74 (d, 1H), 6.66 (dd, 1H), 5.98 (s, 2H), 5.26 (s, 2H), 2.29 (s, 3H) |

TABLE 4

Compounds of the general formula (I) according to the invention, in which Q represents $Q^4$

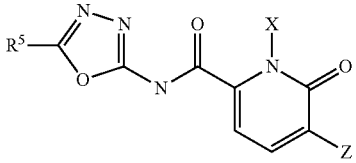

| No. | $R^5$ | X | Z | Physical data ($^1$H-NMR, DMSO-$d_6$, 400 MHz) |
|---|---|---|---|---|
| 4-1 | H | Me | $CF_3$ | |
| 4-2 | Me | Me | $CF_3$ | 8.01 (d, 1H), 6.63 (d, 1H), 3.49 (s, 3H), 2.45 (s, 3H) |
| 4-3 | Et | Me | $CF_3$ | |
| 4-4 | $CH_2OCH_3$ | Me | $CF_3$ | |
| 4-5 | H | Et | $CF_3$ | |
| 4-6 | Me | Et | $CF_3$ | |
| 4-7 | Et | Et | $CF_3$ | |
| 4-8 | $CH_2OCH_3$ | Et | $CF_3$ | |
| 4-9 | H | $CH_2cPr$ | $CF_3$ | |
| 4-10 | Me | $CH_2cPr$ | $CF_3$ | |
| 4-11 | Et | $CH_2cPr$ | $CF_3$ | |
| 4-12 | $CH_2OCH_3$ | $CH_2cPr$ | $CF_3$ | |
| 4-13 | H | $C_2H_4OCH_3$ | $CF_3$ | |
| 4-14 | Me | $C_2H_4OCH_3$ | $CF_3$ | |
| 4-15 | Et | $C_2H_4OCH_3$ | $CF_3$ | |
| 4-16 | $CH_2OCH_3$ | $C_2H_4OCH_3$ | $CF_3$ | |
| 4-17 | H | Bn | $CF_3$ | |
| 4-18 | Me | Bn | $CF_3$ | |
| 4-19 | Et | Bn | $CF_3$ | |
| 4-20 | $CH_2OCH_3$ | Bn | $CF_3$ | |
| 4-21 | H | OMe | $CF_3$ | |
| 4-22 | Me | OMe | $CF_3$ | |
| 4-23 | Et | OMe | $CF_3$ | |
| 4-24 | $CH_2OCH_3$ | OMe | $CF_3$ | |
| 4-25 | H | Me | Cl | |
| 4-26 | Me | Me | Cl | |
| 4-27 | Et | Me | Cl | |
| 4-28 | $CH_2OCH_3$ | Me | Cl | |
| 4-29 | H | Et | Cl | |
| 4-30 | Me | Et | Cl | |
| 4-31 | Et | Et | Cl | |
| 4-32 | $CH_2OCH_3$ | Et | Cl | |
| 4-33 | H | $CH_2cPr$ | Cl | |
| 4-34 | Me | $CH_2cPr$ | Cl | |
| 4-35 | Et | $CH_2cPr$ | Cl | |

TABLE 4-continued

Compounds of the general formula (I) according to the invention, in which Q represents Q⁴

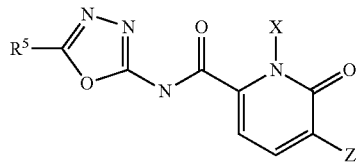

| No. | R⁵ | X | Z | Physical data (¹H-NMR, DMSO-d₆, 400 MHz) |
|---|---|---|---|---|
| 4-36 | CH₂OCH₃ | CH₂cPr | Cl | |
| 4-37 | H | C₂H₄OCH₃ | Cl | |
| 4-38 | Me | C₂H₄OCH₃ | Cl | |
| 4-39 | Et | C₂H₄OCH₃ | Cl | |
| 4-40 | CH₂OCH₃ | C₂H₄OCH₃ | Cl | |
| 4-41 | H | Bn | Cl | |
| 4-42 | Me | Bn | Cl | |
| 4-43 | Et | Bn | Cl | |
| 4-44 | CH₂OCH₃ | Bn | Cl | |
| 4-45 | H | OMe | Cl | |
| 4-46 | Me | OMe | Cl | |
| 4-47 | Et | OMe | Cl | |
| 4-48 | CH₂OCH₃ | OMe | Cl | |
| 4-49 | H | Me | SMe | |
| 4-50 | Me | Me | SMe | |
| 4-51 | Et | Me | SMe | |
| 4-52 | CH₂OCH₃ | Me | SMe | |
| 4-53 | H | Et | SMe | |
| 4-54 | Me | Et | SMe | |
| 4-55 | Et | Et | SMe | |
| 4-56 | CH₂OCH₃ | Et | SMe | |
| 4-57 | H | CH₂cPr | SMe | |
| 4-58 | Me | CH₂cPr | SMe | |
| 4-59 | Et | CH₂cPr | SMe | |
| 4-60 | CH₂OCH₃ | CH₂cPr | SMe | |
| 4-61 | H | C₂H₄OCH₃ | SMe | |
| 4-62 | Me | C₂H₄OCH₃ | SMe | |
| 4-63 | Et | C₂H₄OCH₃ | SMe | |
| 4-64 | CH₂OCH₃ | C₂H₄OCH₃ | SMe | |
| 4-65 | H | Bn | SMe | |
| 4-66 | Me | Bn | SMe | |
| 4-67 | Et | Bn | SMe | |
| 4-68 | CH₂OCH₃ | Bn | SMe | |
| 4-69 | H | OMe | SMe | |
| 4-70 | Me | OMe | SMe | |
| 4-71 | Et | OMe | SMe | |
| 4-72 | CH₂OCH₃ | OMe | SMe | |
| 4-73 | Me | CH₂(3,4-methylenedioxyphenyl) | CF₃ | 8.08 (d, 1H), 6.82 (d, 1H), 6.75 (d, 1H), 6.74 (d, 1H), 6.66 (dd, 1H), 5.97 (s, 2H), 5.29 (s, 2H), 2.47 (s, 3H) |

TABLE 5

Compounds of the general formula (I) according to the invention, in which Q represents Q¹

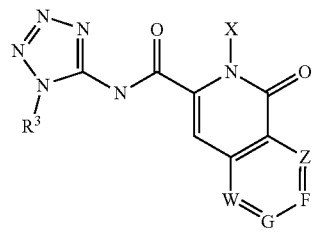

| No. | R³ | X | Z | F | G | W | Physical data (¹H-NMR, DMSO-d₆, 400 MHz) |
|---|---|---|---|---|---|---|---|
| 5-1 | Me | Me | CH | CH | CH | CH | 12.05 (brs, 1H), 8.31 (dd, 1H), 7.83-7.80 (m, 2H), 7.69-7.65 (m, 1H), 7.29 (s, 1H), 4.02 (s, 3H), 3.57 (s, 3H) |

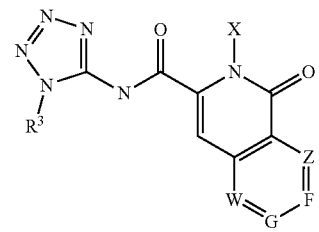

TABLE 5-continued

Compounds of the general formula (I) according to the invention, in which Q represents Q¹

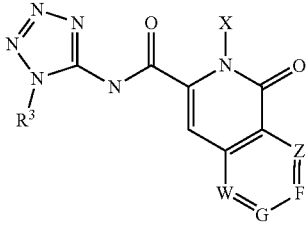 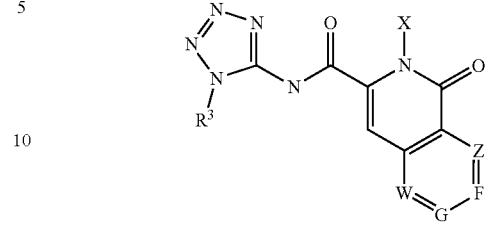

| No. | R³ | X | Z | F | G | W | Physical data (¹H-NMR, DMSO-d₆, 400 MHz) |
|---|---|---|---|---|---|---|---|
| 5-2 | Me | Me | CH | CF | CH | CH | |
| 5-3 | Me | Me | N | CH | CH | CH | 12.15 (brs, 1H), 8.91 (dd, 1H), 8.27 (dd, 1H), 7.80 (dd, 1H), 7.26 (s, 1H), 4.03 (s, 3H), 3.59 (s, 3H) |
| 5-4 | Me | Me | N | CH | CMe | CH | 12.10 (brs, 1H), 8.76 (d, 1H), 8.03 (s, 1H), 7.29 (s, 1H), 4.03 (s, 3H), 3.57 (s, 3H), 2.51 (s, 3H) |
| 5-5 | Me | Me | CH | N | CH | CH | 12.15 (brs, 1H), 9.22 (dd, 1H), 8.80 (d, 1H), 8.10 (ddd, 1H), 7.41 (s, 1H), 4.03 (s, 3H), 3.59 (s, 3H) |
| 5-6 | Me | Me | CH | CH | N | CH | 12.25 (brs, 1H), 9.48 (s, 1H), 8.84 (d, 1H), 7.83 (d, 1H), 7.28 (s, 1H), 4.03 (s, 3H), 3.58 (s, 3H) |
| 5-7 | Me | Me | CH | CH | CH | N | |
| 5-8 | Me | Me | CH | CMe | CH | N | 12.13 (brs, 1H), 8.90 (d, 1H), 8.42 (m, 1H), 7.17 (s, 1H), 4.02 (s, 3H), 3.57 (s, 3H), 2.51 (s, 3H) |
| 5-9 | Me | Me | N | CH | CH | N | 9.07 (d, 1H), 8.95 (d, 1H), 7.32 (s, 1H), 4.04 (s, 3H), 3.60 (s, 3H) |

TABLE 6

Compounds of the general formula (IV) in which R⁶ represents R⁷, and also compounds of the general formula (III) in which R⁶ represents hydrogen and W represents hydrogen

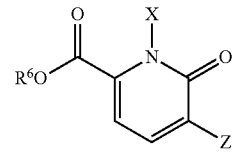

| No. | R⁶ | X | Z | Physical data (¹H-NMR, CDCl₃, 400 MHz) |
|---|---|---|---|---|
| 6-1 | Me | Me | H | 7.48 (dd, 1H), 6.7 (dd, 1H), 6.65 (dd, 1H), 3.87 (s, 3H), 3.51 (s, 3H) |
| 6-2 | H | Me | H | 7.45 (d, 1H), 6.73 (dd, 1H), 6.60 (dd, 1H), 3.39 (s, 3H) |
| 6-3 | Me | Me | CF₃ | 7.74 (d, 1H), 6.76 (d, 1H), 3.97 (s, 3H), 3.72 (s, 3H) |
| 6-4 | H | Me | CF₃ | 7.78 (d, 1H), 6.95 (d, 1H), 3.78 (s, 3H) |
| 6-5 | Et | Et | CF₃ | DMSO-d₆: 7.73 (d, 1H), 6.67 (d, 1H), 4.43 (q, 2H), 4.27 (q, 2H), 1.42 (t, 3H), 1.39 (t, 3H) |
| 6-6 | H | Et | CF₃ | DMSO-d₆: 7.75 (d, 1H), 6.88 (d, 1H), 4.36 (q, 2H), 1.40 (t, 3H) |
| 6-7 | Et | CH₂cPr | CF₃ | 7.73 (d, 1H), 6.67 (d, 1H), 4.43 (q, 2H), 4.27 (d, 2H), 1.42 (t, 3H), 1.21 (m, 1H), 0.51 (m, 2H), 0.41 (m, 2H) |
| 6-8 | H | CH₂cPr | CF₃ | 7.79 (d, 1H), 6.91 (d, 1H), 4.37 (d, 2H), 1.27 (m, 1H), 0.55-0.43 (m, 4H) |
| 6-9 | Et | allyl | CF₃ | 7.74 (d, 1H), 6.70 (d, 1H), 5.89 (m, 1H), 5.23 (m, 1H), 5.17 (m, 1H), 5.01 (m, 2H), 4.37 (q, 2H), 1.39 (t, 3H) |
| 6-10 | H | allyl | CF₃ | 7.79 (d, 1H), 6.92 (d, 1H), 5.94 (m, 1H), 5.26-5.17 (m, 2H), 5.08 (m, 2H) |
| 6-11 | Et | propargyl | CF₃ | 7.74 (d, 1H), 6.81 (d, 1H), 5.27 (d, 2H), 4.45 (q, 2H), 2.28 (t, 1H), 1.43 (t, 3H) |
| 6-12 | H | propargyl | CF₃ | 7.80 (d, 1H), 6.91 (d, 1H), 5.30 (d, 2H), 2.36 (t, 1H) |
| 6-13 | Me | C₂H₄OCH₃ | CF₃ | 7.74 (d, 1H), 6.64 (d, 1H), 4.73 (t, 2H), 3.93 (s, 3H), 3.56 (t, 2H), 3.25 (s, 3H) |
| 6-14 | H | C₂H₄OCH₃ | CF₃ | 7.81 (d, 1H), 6.75 (d, 1H), 4.52 (t, 2H), 3.86 (t, 2H), 3.44 (s, 3H) |
| 6-15 | Me | Bn | CF₃ | 7.75 (d, 1H), 7.32-7.16 (m, 5H), 6.67 (d, 1H), 5.66 (s, 2H), 3.77 (s, 3H) |
| 6-16 | H | Bn | CF₃ | 7.77 (d, 1H), 7.32-7.19 (m, 5H), 6.89 (d, 1H), 5.72 (s, 2H) |
| 6-17 | Et | OMe | CF₃ | 7.72 (d, 1H), 6.49 (d, 1H), 4.45 (q, 2H), 4.22 (s, 3H), 1.42 (t, 3H) |
| 6-18 | H | OMe | CF₃ | DMSO-d₆: 8.01 (d, 1H), 6.63 (d, 1H), 4.07 (s, 3H) |
| 6-19 | Me | Me | Cl | 7.53 (d, 1H), 6.79 (d, 1H), 3.93 (s, 3H), 3.78 (s, 3H) |
| 6-20 | H | Me | Cl | DMSO-d₆: 7.80 (d, 1H), 6.78 (d, 1H), 3.62 (s, 3H) |
| 6-21 | Me | OH | Cl | DMSO-d₆: 7.79 (d, 1H), 6.59 (d, 1H), 3.87 (s, 3H) |

TABLE 6-continued

Compounds of the general formula (IV) in which $R^6$ represents $R^7$, and also compounds of the general formula (III) in which $R^6$ represents hydrogen and W represents hydrogen

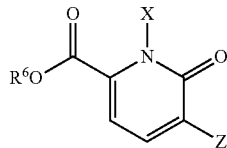

| No. | $R^6$ | X | Z | Physical data ($^1$H-NMR, CDCl$_3$, 400 MHz) |
|---|---|---|---|---|
| 6-22 | Me | OMe | Cl | 7.52 (d, 1H), 6.55 (d, 1H), 4.22 (s, 3H), 3.96 (s, 3H) |
| 6-23 | H | OMe | Cl | 7.54 (d, 1H), 6.60 (d, 1H), 4.20 (s, 3H) |
| 6-24 | Me | Me | Br | 7.75 (d, 1H), 6.70 (d, 1H), 3.93 (s, 3H), 3.78 (s, 3H) |
| 6-25 | H | Me | Br | DMSO-d$_6$: 7.88 (d, 1H), 6.69 (d, 1H), 3.62 (s, 3H) |
| 6-26 | Me | Me | SMe | DMSO-d$_6$: 7.17 (d, 1H), 6.96 (d, 1H), 3.85 (s, 3H), 3.61 (s, 3H), 2.35 (s, 3H) |
| 6-27 | H | Me | SMe | DMSO-d$_6$: 7.15 (d, 1H), 6.94 (d, 1H), 3.62 (s, 3H), 2.35 (s, 3H) |
| 6-28 | Me | Me | SEt | DMSO-d$_6$: 7.23 (d, 1H), 6.93 (d, 1H), 3.84 (s, 3H), 3.60 (s, 3H), 2.88 (q, 2H), 1.27 (t, 3H) |
| 6-29 | H | Me | SEt | DMSO-d$_6$: 7.22 (d, 1H), 6.92 (d, 1H), 3.61 (s, 3H), 2.87 (q, 2H), 1.27 (t, 3H) |

TABLE 7

Compounds of the general formula (IV) in which $R^6$ represents $R^7$, and also compounds of the general formula (III) in which $R^6$ represents hydrogen

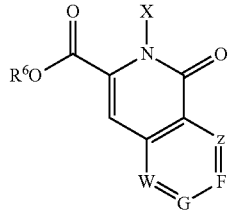

| No. | $R^6$ | X | Z | F | G | W | Physical data ($^1$H-NMR, CDCl$_3$, 400 MHz) |
|---|---|---|---|---|---|---|---|
| 7-1 | Me | Me | CH | CH | CH | CH | 8.45 (m, 1H), 7.67 (m, 1H), 7.62-7.58 (m, 2H), 7.26 (d, 1H), 3.96 (s, 3H), 3.77 (s, 3H) |
| 7-2 | H | Me | CH | CH | CH | CH | DMSO-d$_6$: 8.32 (m, 1H), 7.71-7.69 (m, 2H), 7.59 (m, 1H), 7.29 (s, 1H), 3.72 (s, 3H) |
| 7-3 | Me | Me | N | CH | CH | CH | DMSO-d$_6$: 8.90 (dd, 1H), 8.30 (dd, 1H), 7.77 (dd, 1H), 7.34 (s, 1H), 3.92 (s, 3H), 3.63 (s, 3H) |
| 7-4 | H | Me | N | CH | CH | CH | DMSO-d$_6$: 8.88 (dd, 1H), 8.27 (dd, 1H), 7.75 (dd, 1H), 7.30 (s, 1H), 3.64 (s, 3H) |
| 7-5 | Me | Me | N | CH | CMe | CH | DMSO-d$_6$: 8.75 (m, 1H), 8.06 (m, 1H), 7.24 (s, 1H), 3.91 (s, 3H), 3.61 (s, 3H), 2.46 (s, 3H) |
| 7-6 | H | Me | N | CH | CMe | CH | DMSO-d$_6$: 8.78 (d, 1H), 8.17 (s, 1H), 7.26 (s, 3H), 3.64 (s, 3H), 2.48 (s, 3H) |
| 7-7 | Me | Me | CH | N | CH | CH | DMSO-d$_6$: 9.23 (d, 1H), 8.78 (d, 1H), 8.06 (ddd, 1H), 7.48 (d, 1H), 3.93 (s, 3H), 3.63 (s, 3H) |
| 7-8 | H | Me | CH | N | CH | CH | DMSO-d$_6$: 9.22 (d, 1H), 8.78 (d, 1H), 8.05 (ddd, 1H), 7.45 (d, 1H), 3.65 (s, 3H) |
| 7-9 | Me | Me | CH | CH | N | CH | DMSO-d$_6$: 9.40 (t, 1H), 8.82 (d, 1H), 7.76 (dd, 1H), 7.29 (d, 1H), 3.93 (s, 3H), 3.60 (s, 3H) |
| 7-10 | H | Me | CH | CH | N | CH | DMSO-d$_6$: 9.39 (s, 1H), 8.80 (d, 1H), 7.74 (dd, 1H), 7.24 (d, 1H), 3.61 (s, 3H) |
| 7-11 | Me | Me | CH | CMe | CH | N | DMSO-d$_6$: 8.88 (dd, 1H), 8.39 (m, 1H), 7.24 (d, 1H), 3.92 (s, 3H), 3.61 (s, 3H), 2.48 (s, 3H) |
| 7-12 | H | Me | CH | CMe | CH | N | DMSO-d$_6$: 8.86 (dd, 1H), 8.38 (m, 1H), 7.20 (d, 1H), 3.63 (s, 3H), 2.45 (d, 3H) |
| 7-13 | Me | Me | N | CH | CH | N | DMSO-d$_6$: 9.05 (d, 1H), 8.94 (d, 1H), 7.24 (d, 1H), 3.94 (s, 3H), 3.63 (s, 3H) |
| 7-14 | H | Me | N | CH | CH | N | DMSO-d$_6$: 9.03 (d, 1H), 8.92 (d, 1H), 7.18 (d, 1H), 3.65 (s, 3H) |

B. FORMULATION EXAMPLES a) A dusting product is obtained by mixing 10 parts by weight of a compound of the formula (I) and/or salts thereof and 90 parts by weight of talc as inert substance and comminuting the mixture in a hammer mill.

b) A readily water-dispersible, wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

c) A readily water-dispersible dispersion concentrate is obtained by mixing 20 parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.

d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.

e) Water-dispersible granules are obtained by mixing
75 parts by weight of a compound of the formula (I) and/or salts thereof,
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill and granulating the powder in a fluidized bed by spraying on water as a granulating liquid.

f) Water-dispersible granules are also obtained by homogenizing and precomminuting
25 parts by weight of a compound of the formula (I) and/or salts thereof,
5 parts by weight of sodium 2,2'-dinaphthylmethane-6,6'-disulfonate,
2 parts by weight of sodium oleoylmethyltaurate,
1 part by weight of polyvinyl alcohol,
17 parts by weight of calcium carbonate and
50 parts by weight of water
in a colloid mill, then grinding the mixture in a bead mill and atomizing and drying the resulting suspension in a spray tower by means of a one-phase nozzle.

C. BIOLOGICAL EXAMPLES

1. Pre-Emergence Herbicidal Action Against Weed Plants

Seeds of monocotyledonous and dicotyledonous weed plants and crop plants are placed in wood-fiber pots in sandy loam and covered with soil. The compounds according to the invention, formulated in the form of wettable powders (WP) or as emulsion concentrates (EC), are then applied as aqueous suspension or emulsion at a water application rate of 600 to 800 l/ha (converted) with the addition of 0.2% of wetting agent to the surface of the covering soil. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants). Here, for example, the compounds Nos. 1-03, 1-19, 3-01, 3-02, 1-31, 1-23, 1-04, 1-24 and 1-11, at an application rate of 320 g/ha, each show an activity of at least 80% against *Echinochloa crus galli, Setaria viridis, Abutilon theophrasti, Amaranthus retroflexus* and *Veronica persica*.

2. Post-Emergence Herbicidal Action Against Weed Plants

Seeds of monocotyledonous and dicotyledonous weed and crop plants are placed in sandy loam in wood-fiber pots, covered with soil and cultivated in a greenhouse under good growth conditions. 2 to 3 weeks after sowing, the test plants are treated at the one-leaf stage. The compounds according to the invention, formulated in the form of wettable powders (WP) or as emulsion concentrates (EC), are then sprayed as aqueous suspension or emulsion at a water application rate of 600 to 800 l/ha (converted) with the addition of 0.2% of wetting agent onto the green parts of the plants. After the test plants have been left to stand in the greenhouse under optimal growth conditions for about 3 weeks, the action of the formulations is assessed visually in comparison to untreated controls (herbicidal action in percent (%): 100% action=the plants have died, 0% action=like control plants). Here, for example, the compounds Nos. 1-03, 1-19, 3-01, 3-02, 1-31, 1-23, 1-04, 1-24 and 1-11, at an application rate of 80 g/ha, each show an activity of at least 80% against *Echinochloa crus galli, Amaranthus retroflexus, Matricaria inodora, Stellaria media, Viola tricolor* and *Veronica persica*.

The invention claimed is:

1. A 6-pyridon-2-carbamoylazole of the formula (I) or a salt thereof

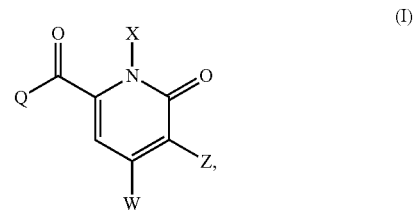

in which
Q represents a radical $Q^1$, $Q^2$, $Q^3$ or $Q^4$,

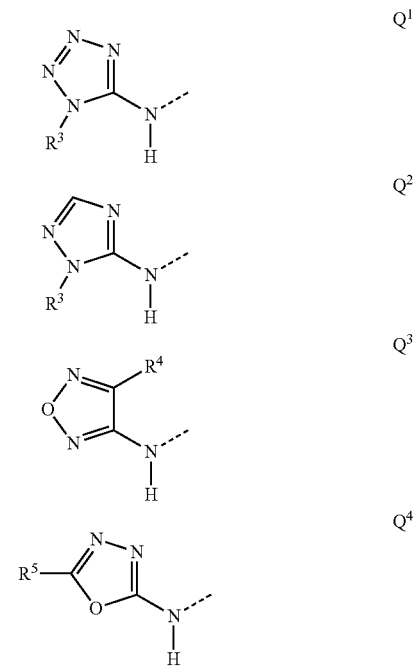

$R^3$ represents $(C_1-C_8)$-alkyl, $(C_2-C_8)$-alkenyl, $(C_2-C_8)$-alkynyl, where these radicals are each substituted by s radicals from the group consisting of halogen, cyano, hydroxy, nitro, $SiR^{10}{}_3$, $PO(OR^{10})_2$, $S(O)_n$—$(C_1-C_6)$- alkyl, $(C_1-C_6)$-alkoxy, halo-$(C_1-C_6)$-alkoxy, $COR^{3a}$, $COOR^{3a}$, $OCOR^{3a}$, $NR^{3a}COR^{3a}$, $NR^{3a}SO_2R^{3b}$, $(C_3-C_6)$-cycloalkyl, heteroaryl, heterocyclyl or phenyl, where the 4 last-mentioned radicals are each substituted by p radicals from the group consisting of methyl, ethyl, methoxy, trifluoromethyl, cyano and halogen, and where heterocyclyl carries n oxo groups, or $R^3$ represents phenyl which is substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{3a}$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^{3b}$ represents $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^4$ represents hydrogen, $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, $(C_2-C_6)$-alkenyl, $(C_2-C_6)$-alkenyloxy, $(C_2-C_6)$-haloalkenyl, $(C_2-C_6)$-alkynyl, $(C_2-C_6)$-alkynyloxy, $(C_2-C_6)$-haloalkynyl, $(C_1-C_6)$-alkoxy-$(C_1-C_6)$-alkyl, cyano, nitro, methylsulfenyl, methylsulfinyl, methylsulfonyl, acetylamino, benzoylamino, methoxycarbonyl, ethoxycarbonyl, methoxycarbonylmethyl, ethoxycarbonylmethyl, benzoyl, methylcarbonyl, piperidinylcarbonyl, trifluoromethylcarbonyl, halogen, amino, aminocarbonyl, methylaminocarbonyl, dimethylaminocarbonyl, methoxymethyl, or represents heteroaryl, heterocyclyl or phenyl, each of which is substituted by p radicals from the group consisting of methyl, ethyl, methoxy, trifluoromethyl and halogen, $R^5$ represents hydrogen, $(C_1-C_6)$-alkyl, $(C_1-C_6)$-alkoxy-$(C_1-C_6)$-alkyl, $CH_2R^{5a}$, $(C_3-C_7)$-cycloalkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $OR^6$, $NHR^6$, methoxycarbonyl, ethoxycarbonyl, methoxycarbonylmethyl, ethoxycarbonylmethyl, methylcarbonyl, trifluoromethylcarbonyl, dimethylamino, acetylamino, methylsulfenyl, methylsulfinyl, methylsulfonyl or represents heteroaryl, heterocyclyl, benzyl or phenyl, each of which is substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^{5a}$ represents acetoxy, acetamido, N-methylacetamido, benzoyloxy, benzamido, N-methylbenzamido, methoxycarbonyl, ethoxycarbonyl, benzoyl, methylcarbonyl, piperidinylcarbonyl, morpholinylcarbonyl, trifluoromethylcarbonyl, aminocarbonyl, methylaminocarbonyl, dimethylaminocarbonyl, $(C_1-C_6)$-alkoxy, $(C_3-C_6)$-cycloalkyl, or represents heteroaryl or heterocyclyl, each of which is substituted by p radicals from the group consisting of methyl, ethyl, methoxy, trifluoromethyl and halogen, X represents $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $OCOOR^6$, $OC(O)N(R^6)_2$, $OR^6$, $OCOR^6$, $OSO_2R^7$, $(C_1-C_6)$-alkyl-$S(O)_nR^7$, $(C_1-C_6)$-alkyl-$OR^6$, $(C_1-C_6)$-alkyl-$OCOR^6$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-CN, $(C_1-C_6)$-alkyl-$SO_2N(R^6)_2$, $(C_1-C_6)$-alkyl-$NR^6COR^6$, $(C_1-C_6)$-alkyl-$NR^6SO_2R^7$, $CH_2P(O)(OR^{10})_2$, $(C_1-C_6)$-alkyl-aryl, $(C_1-C_6)$-alkyl-heteroaryl, $(C_1-C_6)$-alkyl-heterocyclyl, where the three last-mentioned radicals are each substituted by s radicals from the group consisting of halogen, cyano, nitro, $(C_1-C_6)$-alkyl, halo-$(C_1-C_6)$-alkyl, $S(O)_n$—$(C_1-C_6)$-alkyl, $(C_1-C_6)$-alkoxy, halo-$(C_1-C_6)$-alkoxy, and where heterocyclyl carries n oxo groups, Z represents hydrogen, halogen, cyano, thiocyanato, nitro, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_1-C_6)$-alkyl-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^E$, $COOR^6$, $OR^6$, $OCOOR^6$, $NR^6COOR^6$, $C(O)N(R^6)_2$, $NR^6C(O)N(R^6)_2$, $OC(O)N(R^6)_2$, $C(O)NR^6OR^6$, $OSO_2R^7$, $S(O)_nR^7$, $SO_2OR^6$, $SO_2N(R^6)_2$, $NR^6SO_2R^7$, $NR^6COR^6$, $(C_1-C_6)$-alkyl-$S(O)_nR^7$, $(C_1-C_6)$-alkyl-$OR^6$, $(C_1-C_6)$-alkyl-$OCOR^1$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^1SO_2R^7$, $N(R^6)_2$, $P(O)(OR^{10})_2$, heteroaryl, heterocyclyl or phenyl, where the three last-mentioned radicals are each substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy or halo-$(C_1-C_6)$-alkoxy, and where heterocyclyl carries n oxo groups, W represents hydrogen, halogen, $(C_1-C_4)$-alkyl, $(C_1-C_4)$-haloalkyl, $S(O)_nR^{10}$, or Z and W together with the carbon atoms to which they are attached form a five- or six-membered aromatic ring system in which p carbon atoms are replaced by heteroatoms from the group consisting of N, O and S, and which is substituted by q radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_6)$-alkyl, $R^6$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkenyl, $(C_1-C_6)$-alkyl-O-$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocycyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^8$-heteroaryl, $(C_1-C_6)$-alkyl-$NR^8$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^7$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO_2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^9$ represents $(C_1-C_6)$-alkyl, $(C_2-C_6)$-alkenyl, $(C_2-C_6)$-alkynyl or phenyl, $R^{10}$ represents $(C_1-C_4)$-alkyl, n represents 0, 1 or 2, p represents 0, 1, 2 or 3, q represents 0, 1, 2, 3 or 4, s represents 0, 1, 2, 3, 4 or 5.

2. The 6-pyridone-2-carbamoylazole or salt as claimed in claim 1 in which

Q represents a radical $Q^1$, $Q^2$, $Q^3$ or $Q^4$,

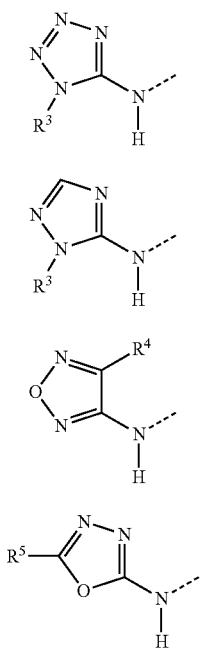

$R^3$ represents $(C_1-C_8)$-alkyl, $(C_2-C_8)$-alkenyl, $(C_2-C_8)$-alkynyl, where these radicals are each substituted by s radicals from the group consisting of halogen, cyano, nitro, $S(O)_n$—$(C_1-C_6)$-alkyl, $(C_1-C_6)$-alkoxy, halo-$(C_1-C_6)$-alkoxy, $(C_3-C_6)$-cycloalkyl, heteroaryl, heterocyclyl or phenyl, where the 4 last-mentioned radicals are each substituted by p radicals from the group consisting of methyl, ethyl, methoxy, trifluoromethyl, cyano and halogen, and where heterocyclyl carries n oxo groups, or $R^3$ represents phenyl which is in each case substituted by p radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy, halo-$(C_1-C_6)$-alkoxy and $(C_1-C_6)$-alkoxy-$(C_1-C_4)$-alkyl, $R^4$ represents $(C_1-C_6)$-alkyl, $(C_3-C_7)$-cycloalkyl, halo-$(C_1-C_6)$-alkyl, $(C_1-C_6)$-alkoxy, halo-$(C_1-C_6)$-alkoxy, cyano, nitro, methylsulfenyl, methylsulfinyl, methylsulfonyl, $(C_1-C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1-yl, pyrazol-1-yl, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or phenyl, wherein the phenyl is in each case substituted by p radicals from the group consisting of methyl, ethyl, methoxy, trifluoromethyl and halogen, $R^5$ represents hydrogen, $(C_1-C_6)$-alkyl, $(C_3-C_7)$-cycloalkyl, halo-$(C_1-C_6)$-alkyl, $(C_3-C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or phenyl, wherein the phenyl is substituted by p radicals from the group consisting of methyl, methoxy, trifluoromethyl and halogen, X represents $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_3-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $OCOOR^6$, $OC(O)N(R^6)_2$, $OR^6$, $OCOR^6$, $OSO_2R^7$, $(C_1-C_6)$-alkyl-$S(O)_nR^7$, $(C_1-C_6)$-alkyl-$OR^6$, $(C_1-C_6)$-alkyl-$OCOR^6$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^6SO_2R^7$, $CH_2P(O)(OR^{10})_2$, $(C_1-C_6)$-alkyl-aryl, $(C_1-C_6)$-alkyl-heteroaryl, $(C_1-C_6)$-alkyl-heterocyclyl, where the three last-mentioned radicals are each substituted by s radicals from the group consisting of halogen, cyano, nitro, $(C_1-C_6)$-alkyl, halo-$(C_1-C_6)$-alkyl, $S(O)_n$—$(C_1-C_6)$-alkyl, $(C_1-C_6)$-alkoxy and halo-$(C_1-C_6)$-alkoxy, and where heterocyclyl carries n oxo groups, Z represents hydrogen, halogen, cyano, thiocyanato, nitro, $(C_1-C_6)$-alkyl, halo-$(C_1-C_6)$-alkyl, $(C_2-C_6)$-alkenyl, halo-$(C_2-C_6)$-alkenyl, $(C_2-C_6)$-alkynyl, halo-$(C_2-C_6)$-alkynyl, $(C_3-C_6)$-cycloalkyl, halo-$(C_3-C_6)$-cycloalkyl, $(C_3-C_6)$-cycloalkyl-$(C_1-C_6)$-alkyl, halo-$(C_3-C_6)$-cycloalkyl-$(C_1-C_6)$-alkyl, $COR^E$, $COOR^6$, $OCOOR^6$, $NR^6COOR^6$, $C(O)N(R^6)_2$, $NR^6C(O)N(R^6)_2$, $OC(O)N(R^6)_2$, $C(O)NR^6OR^6$, $OSO_2R^7$, $S(O)_nR^7$, $SO_2OR^6$, $SO_2N(R^6)_2$, $NR^6SO_2R^7$, $NR^6COR^6$, $(C_1-C_6)$-alkyl-$S(O)_nR^7$, $(C_1-C_6)$-alkyl-$OR^6$, $(C_1-C_6)$-alkyl-$OCOR^1$, $(C_1-C_6)$-alkyl-$OSO_2R^7$, $(C_1-C_6)$-alkyl-$CO_2R^6$, $(C_1-C_6)$-alkyl-$SO_2OR^6$, $(C_1-C_6)$-alkyl-$CON(R^6)_2$, $(C_1-C_6)$-alkyl-$SO_2N(R^6)_2$, $(C_1-C_6)$-alkyl-$NR^6COR^6$, $(C_1-C_6)$-alkyl-$NR^1SO_2R^7$, $N(R^6)_2$, $P(O)(OR^{10})_2$, heteroaryl, heterocyclyl or phenyl, where the last three radicals are in each case substituted by s radicals from the group consisting of halogen, nitro, cyano, $(C_1-C_6)$-alkyl, halo-$(C_1-C_6)$-alkyl, $(C_3-C_6)$-cycloalkyl, $S(O)_n$—$(C_1-C_6)$-alkyl, $(C_1-C_6)$-alkoxy and halo-$(C_1-C_6)$-alkoxy, and where heterocyclyl carries n oxo groups, W represents hydrogen, halogen, methyl, trifluoromethyl, $S(O)_n$Me, or Z and W together with the carbon atoms to which they are attached form a five- or six-membered aromatic ring system in which p carbon atoms are replaced by heteroatoms from the group consisting of N, O and S, and which is substituted by q radicals from the group consisting of halogen, nitro, cyano, $(C_1-C_6)$-alkyl, halo-$(C_1-C_4)$-alkyl, $(C_3-C_6)$-cycloalkyl, $S(O)_n$—$(C_1-C_6)$-alkyl, $(C_1-C_6)$-alkoxy-$(C_1-C_6)$-alkyl, $(C_1-C_6)$-alkoxy and halo-$(C_1-C_6)$-alkoxy, $R^6$ represents hydrogen, $(C_1\text{-}C_6)$-alkyl, $(C_1\text{-}C_6)$-haloalkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_3\text{-}C_6)$-cycloalkyl, $(C_3\text{-}C_6)$-cycloalkenyl, $(C_3\text{-}C_6)$-halocycloalkyl, $(C_1\text{-}C_6)$-alkyl-O—$(C_1\text{-}C_6)$-alkyl, $(C_3\text{-}C_6)$-cycloalkyl-$(C_1\text{-}C_6)$-alkyl, phenyl, phenyl-$(C_1\text{-}C_6)$-alkyl, heteroaryl, $(C_1\text{-}C_6)$-alkyl-heteroaryl, heterocycyl, $(C_1\text{-}C_6)$-alkyl-heterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^8$-heteroaryl, $(C_1\text{-}C_6)$-alkyl-$NR^8$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO2R^9$, $CO_2R^8$, $COSR^9$, $CON(R^8)_2$ and $(C_1\text{-}C_4)$-alkoxy-$(C_2\text{-}C_6)$-alkoxycarbonyl, and where heterocyclyl carries n oxo groups, $R^7$ represents $(C_1\text{-}C_6)$-alkyl, $(C_1\text{-}C_6)$-haloalkyl, $(C_2\text{-}C_6)$-alkenyl, $(C_2\text{-}C_6)$-haloalkenyl, $(C_2\text{-}C_6)$-alkynyl, $(C_2\text{-}C_6)$-haloalkynyl, $(C_3\text{-}C_6)$-cycloalkyl, $(C_3\text{-}C_6)$-cycloalkenyl, $(C_3\text{-}C_6)$-halocycloalkyl, $(C_1\text{-}C_6)$-alkyl-O—$(C_1\text{-}C_6)$-alkyl, $(C_3\text{-}C_6)$-cycloalkyl-$(C_1\text{-}C_6)$-alkyl, phenyl, phenyl-$(C_1\text{-}C_6)$-alkyl, heteroaryl, $(C_1\text{-}C_6)$-alkylheteroaryl, heterocyclyl, $(C_1\text{-}C_6)$-alkylheterocyclyl, $(C_1\text{-}C_6)$-alkyl-O-heteroaryl, $(C_1\text{-}C_6)$-alkyl-O-heterocyclyl, $(C_1\text{-}C_6)$-alkyl-$NR^3$-heteroaryl, $(C_1\text{-}C_6)$-alkyl-$NR^3$-heterocyclyl, where the 21 last-mentioned radicals are substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO_2R^9$, $CO_2R^8$, $COSR^9$, $CON(R^8)_2$ and $(C_1\text{-}C_4)$-alkoxy-$(C_2\text{-}C_6)$-alkoxycarbonyl, and where heterocyclyl carries n oxo groups, $R^8$ represents hydrogen, $(C_1\text{-}C_6)$-alkyl, $(C_2\text{-}C_6)$-alkenyl, $(C_2\text{-}C_6)$-alkynyl, $(C_3\text{-}C_6)$-cycloalkyl, $(C_3\text{-}C_6)$-cycloalkyl-$(C_1\text{-}C_6)$-alkyl or phenyl, $R^9$ represents $(C_1\text{-}C_6)$-alkyl, $(C_2\text{-}C_6)$-alkenyl, $(C_2\text{-}C_6)$-alkynyl or phenyl, $R^{10}$ represents $(C_1\text{-}C_4)$-alkyl, n represents 0, 1 or 2, p represents 0, 1, 2 or 3, q represents 0, 1, 2, 3 or 4, s represents 0, 1, 2, 3, 4 or 5.

3. The 6-pyridone-2-carbamoylazole or salt as claimed in claim 1 in which

Q represents a radical $Q^1$, $Q^2$, $Q^3$ or $Q^4$,

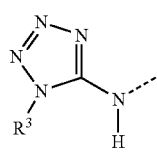

$Q^1$

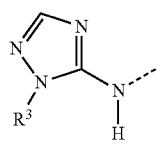

$Q^2$

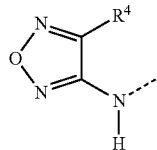

$Q^3$

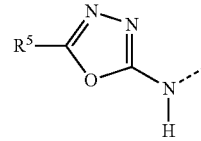

$Q^4$ $R^3$ represents $(C_1\text{-}C_8)$-alkyl, $(C_2\text{-}C_8)$-alkenyl or $(C_2\text{-}C_8)$-alkynyl, each of which is substituted by s radicals from the group consisting of halogen, cyano, nitro, $S(O)_n$—$(C_1\text{-}C_6)$-alkyl, $(C_1\text{-}C_6)$-alkoxy and halo-$(C_1\text{-}C_6)$-alkoxy, $R^4$ represents $(C_1\text{-}C_6)$-alkyl, $(C_3\text{-}C_7)$-cycloalkyl, halo-$(C_1\text{-}C_6)$-alkyl, $(C_1\text{-}C_6)$-alkoxy, halo-$(C_1\text{-}C_6)$-alkoxy, cyano, nitro, methylsulfenyl, methylsulfinyl, methylsulfonyl, $(C_1\text{-}C_4)$-alkylcarbonylamino, benzoylamino, methoxycarbonyl, ethoxycarbonyl, benzoyl, phenoxy, methylcarbonyl, piperidinylcarbonyl, trifluoromethylcarbonyl, halogen, amino, aminocarbonyl, methylaminocarbonyl, dimethylaminocarbonyl, methoxymethyl, 1,2,4-triazol-1H, 1-pyrazol-1H, 2-thiophenyl, 2-pyridinyl, 3-pyridinyl, 4-pyridinyl, 1,2,4-oxadiazol-3-yl, benzoxazol-2-yl, 1-ethylbenzimidazol-2-yl, piperidin-1-yl, or represents phenyl, wherein the phenyl which is in each case substituted by s radicals from the group consisting of methyl, ethyl, methoxy, trifluoromethyl and halogen, $R^5$ represents hydrogen, $(C_1\text{-}C_6)$-alkyl, $(C_3\text{-}C_7)$-cycloalkyl, halo-$(C_1\text{-}C_6)$-alkyl, $(C_3\text{-}C_7)$-cycloalkylmethyl, methoxycarbonylmethyl, ethoxycarbonylmethyl, acetylmethyl, methoxymethyl, methoxyethyl, benzyl, pyrazin-2-yl, furan-2-yl, tetrahydrofuran-2-yl, morpholine, dimethylamino, or phenyl, wherein the phenyl is substituted by p radicals from the group consisting of methyl, methoxy, trifluoromethyl and halogen, X represents $(C_1\text{-}C_6)$-alkyl, halo-$(C_1\text{-}C_6)$-alkyl, $(C_3\text{-}C_6)$-cycloalkyl, $OR^6$, $S(O)_nR^7$, $(C_1\text{-}C_6)$-alkyl-$S(O)_nR^7$, $(C_1\text{-}C_6)$-alkyl-$OR^6$, $(C_1\text{-}C_6)$-alkyl-$CON(R^6)_2$, $(C_1\text{-}C_6)$-alkyl-$SO_2N(R^6)_2$, $(C_1\text{-}C_6)$-alkyl-$NR^6COR^6$, $(C_1\text{-}C_6)$-alkyl-$NR^6SO_2R^7$, $(C_1\text{-}C_6)$-alkyl-heteroaryl, $(C_1\text{-}C_6)$-alkylheterocyclyl, where the two last-mentioned radicals are in each case substituted by s radicals from the group consisting of halogen, $(C_1\text{-}C_6)$-alkyl, halo-$(C_1\text{-}C_6)$-alkyl, $S(O)_n$—$(C_1\text{-}C_6)$-alkyl, $(C_1\text{-}C_6)$-alkoxy and halo-$(C_1\text{-}C_6)$-alkoxy, and where heterocyclyl carries n oxo groups, Z represents hydrogen, halogen, cyano, thiocyanato, nitro, $(C_1\text{-}C_6)$-alkyl, halo-$(C_1\text{-}C_6)$-alkyl, $(C_2\text{-}C_6)$-alkenyl, halo-$(C_2\text{-}C_6)$-alkenyl, $(C_2\text{-}C_6)$-alkynyl, halo-$(C_2\text{-}C_6)$-alkynyl, $(C_3\text{-}C_6)$-cycloalkyl, halo-$(C_3\text{-}C_6)$-cycloalkyl, $(C_3\text{-}C_6)$-cycloalkyl-$(C_1\text{-}C_6)$-alkyl, halo-$(C_3\text{-}C_6)$-cycloalkyl-$(C_1\text{-}C_6)$-alkyl, $COR^6$, $COOR^6$, $OCOOR^6$, $NR^6COOR^6$, $C(O)N(R^6)_2$, $NR^6C(O)N(R^6)_2$, $OC(O)N(R^6)_2$, $C(O)NR^6OR^6$, $OSO_2R^7$, $S(O)_nR^7$, $SO_2OR^6$, $SO_2N(R^6)_2$, $NR^6SO2R^7$, $NR^6COR^6$, $(C_1\text{-}C_6)$-alkyl-$S(O)_nR^7$, $(C_1\text{-}C_6)$-alkyl-$OR^6$, $(C_1\text{-}C_6)$-alkyl-$OCOR^1$, $(C_1\text{-}C_6)$-alkyl-$OSO_2R^7$, $(C_1\text{-}C_6)$-alkyl-$CO_2R^6$, $(C_1\text{-}C_6)$-alkyl-$SO_2OR^6$, $(C_1\text{-}C_6)$-alkyl-$CON(R^6)_2$, $(C_1\text{-}C_6)$-alkyl-$SO_2N(R^6)_2$, $(C_1\text{-}C_6)$-alkyl-$NR^6COR^6$, $(C_1\text{-}C_6)$-alkyl-$NR^1SO_2R^7$, $N(R^6)_2$, $P(O)(OR^{10})_2$, heteroaryl, heterocyclyl or phenyl, where the 3 last-mentioned radicals are in each case substituted by s radicals from the group consisting of halogen, nitro, cyano, $(C_1\text{-}C_6)$-alkyl, halo-$(C_1\text{-}C_6)$-alkyl, $(C_3\text{-}C_6)$-cycloalkyl, $S(O)_n$—$(C_1\text{-}C_6)$-alkyl, $(C_1\text{-}C_6)$-alkoxy and halo-$(C_1\text{-}C_6)$-alkoxy, and where heterocyclyl carries n oxo groups, W represents hydrogen, chlorine, methyl or trifluoromethyl, or Z and W together with the carbon atoms to which they are attached form a five- or six-membered aromatic ring system in which p carbon atoms are replaced by heteroatoms from the group consisting of N, O and S, and which is substituted by q radicals from the group consisting of halogen, nitro, cyano, $(C_1-C_6)$-alkyl, halo-$(C_1-C_4)$-alkyl, $S(O)_n$—$(C_1-C_6)$-alkyl, $(C_1-C_6)$-alkoxy-methyl, $(C_1-C_6)$-alkoxy and halo-$(C_1-C_6)$-alkoxy, $R^6$ represents hydrogen, $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkyl-heteroaryl, heterocycyl, $(C_1-C_6)$-alkyl-heterocyclyl, $(C_1-C_6)$-alkyl-O-heteroaryl, $(C_1-C_6)$-alkyl-O-heterocyclyl, $(C_1-C_6)$-alkyl-$NR^8$-heteroaryl, $(C_1-C_6)$-alkyl-$NR^8$-heterocyclyl, where the 21 last-mentioned radicals are in each case substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^7$ represents $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl, $(C_2-C_6)$-haloalkynyl, $(C_3-C_6)$-cycloalkyl, $(C_3-C_6)$-cycloalkenyl, $(C_3-C_6)$-halocycloalkyl, $(C_1-C_6)$-alkyl-O—$(C_1-C_6)$-alkyl, $(C_3-C_6)$-cycloalkyl-$(C_1-C_6)$-alkyl, phenyl, phenyl-$(C_1-C_6)$-alkyl, heteroaryl, $(C_1-C_6)$-alkylheteroaryl, heterocyclyl, $(C_1-C_6)$-alkylheterocyclyl, $(C_1-C_6)$-alkyl-O-heteroaryl, $(C_1-C_6)$-alkyl-O-heterocyclyl, $(C_1-C_6)$-alkyl-$NR^3$-heteroaryl, $(C_1-C_6)$-alkyl-$NR^3$-heterocyclyl, where the 21 last-mentioned radicals are each substituted by s radicals from the group consisting of cyano, halogen, nitro, thiocyanato, $OR^8$, $S(O)_nR^9$, $N(R^8)_2$, $NR^8OR^8$, $COR^8$, $OCOR^8$, $SCOR^9$, $NR^8COR^8$, $NR^8SO_2R^9$, $CO_2R^8$, $COSR^9$, $CON(R^8)_2$ and $(C_1-C_4)$-alkoxy-$(C_2-C_6)$-alkoxycarbonyl, and where heterocyclyl carries n oxo groups, $R^8$ represents hydrogen, $(C_1-C_6)$-alkyl, $(C_2-C_6)$-alkenyl, $(C_2-C_6)$-alkynyl, $(C_3-C_6)$-cycloalkyl, $(C_3-C_6)$-cycloalkyl-$(C_1-C_6)$-alkyl or phenyl, $R^9$ represents $(C_1-C_6)$-alkyl, $(C_2-C_6)$-alkenyl, $(C_2-C_6)$-alkynyl or phenyl, $R^{10}$ represents $(C_1-C_4)$-alkyl, n represents 0, 1 or 2, p represents 0, 1, 2 or 3, q represents 0, 1, 2, 3 or 4, s represents 0, 1, 2, 3, 4 or 5.

4. A herbicidal composition which comprises a herbicidally effective amount of at least one compound as claimed in claim 1.

5. The herbicidal composition as claimed in claim 4 in a mixture with one or more formulation auxiliaries.

6. The herbicidal composition as claimed in claim 4, comprising at least one further substance selected from the group consisting of insecticides, acaricides, herbicides, fungicides, safeners and growth regulators.

7. The herbicidal composition as claimed in claim 6, comprising a safener.

8. The herbicidal composition as claimed in claim 7, comprising cyprosulfamide, cloquintocet-mexyl, mefenpyr-diethyl or isoxadifen-ethyl.

9. The herbicidal composition as claimed in claim 6, comprising a further herbicide.

10. A method for controlling unwanted plants, comprising applying an effective amount of at least one compound as claimed in claim 1 to one or more plants or to a site of unwanted plants.

11. A compound as claimed in claim 1 capable of being used for controlling unwanted plants.

12. A method as claimed in claim 10, wherein the compound of formula (I) is used for controlling one or more unwanted plants in one or more crops of one or more useful plants.

13. The method as claimed in claim 12, wherein the useful plants are transgenic useful plants.

14. The compound as claimed in claim 1, wherein Q is a radical $Q^1$,

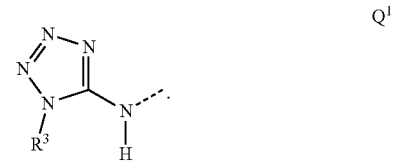

15. The compound as claimed in claim 1, wherein Q is a radical $Q^2$,

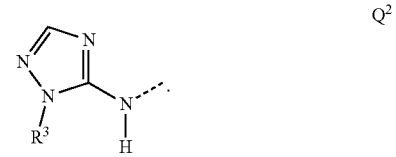

16. The compound as claimed in claim 1, wherein Q is a radical $Q^3$,

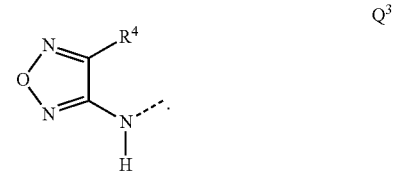

17. The compound as claimed in claim 1, wherein Q is a radical $Q^4$,

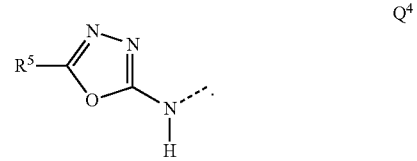

18. The compound as claimed in claim 1, wherein Z is $CF_3$.

19. The compound as claimed in claim 18, wherein Q is a radical $Q^1$,
20. The compound as claimed in claim 18, wherein Q is a radical $Q^3$,
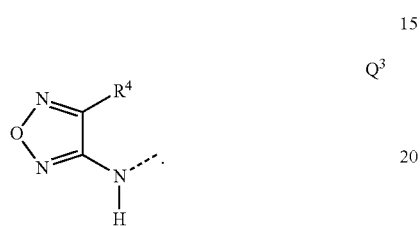
* * * * *